US009554750B2

(12) United States Patent
Quackenbush et al.

(10) Patent No.: US 9,554,750 B2
(45) Date of Patent: Jan. 31, 2017

(54) MOTILITY MANOMETER PRIMING MANIFOLD SYSTEM WITH ICON-BASED USER INTERFACE AND WIRELESS CONNECTIVITY

(71) Applicant: MedSpira LLC, Minneapolis, MN (US)

(72) Inventors: Jim Quackenbush, Chanhassen, MN (US); Steve Remy, New York, NY (US)

(73) Assignee: MEDSPIRA LLC, Minneapolis, MN (US)

( * ) Notice: Subject to any disclaimer, the term of this patent is extended or adjusted under 35 U.S.C. 154(b) by 136 days.

(21) Appl. No.: 13/745,274

(22) Filed: Jan. 18, 2013

(65) Prior Publication Data

US 2013/0184612 A1    Jul. 18, 2013

Related U.S. Application Data

(60) Provisional application No. 61/588,163, filed on Jan. 18, 2012, provisional application No. 61/588,168, filed on Jan. 18, 2012.

(51) Int. Cl.
  *A61B 5/00*  (2006.01)
  *A61B 5/107*  (2006.01)
  (Continued)

(52) U.S. Cl.
  CPC ........... *A61B 5/6847* (2013.01); *A61B 5/0002* (2013.01); *A61B 5/035* (2013.01); *A61B 5/036* (2013.01);
  (Continued)

(58) Field of Classification Search
  None
  See application file for complete search history.

(56) References Cited

U.S. PATENT DOCUMENTS 4,600,015 A    7/1986    Evans et al.
4,739,767 A    4/1988    Lahr
              (Continued)

FOREIGN PATENT DOCUMENTS

FR         2673524         9/1992
WO    WO2011014530 A2    2/2011

OTHER PUBLICATIONS

Apr. 29, 2013, International Search Report and Written Opinion from PCT Application No. PCT/US2013/022217, 14 pages.
(Continued)

*Primary Examiner* — Devin Henson
*Assistant Examiner* — Matthew Kremer
(74) *Attorney, Agent, or Firm* — Hollingsworth Davis, LLC

(57) ABSTRACT

A catheter includes a distal distension balloon and circumferentially arranged motility measurement balloons proximal of the distension balloon. A manifold includes balloon ports each configured to fluidly couple to a motility measurement balloon, pressure transducer ports, and a priming port. A port selector is coupled to the manifold and movable between different positions. Each port selector position causes the manifold to establish different fluidic couplings between the respective motility balloon, pressure transducer, and priming ports. A pressure sensing device includes pressure transducers each fluidly coupled to one of the pressure transducer ports. The pressure sensing device is configured to coordinate calibration of the pressure transducers at atmospheric pressure with the port selector in a first position and motility balloon pressure measurements with the port selector in a third position. Priming of the motility measurement balloons is implemented by moving the port selector to a second position.

13 Claims, 20 Drawing Sheets

(51) Int. Cl.
*A61M 39/22* (2006.01)
*A61B 5/03* (2006.01)
*A61B 5/20* (2006.01)

(52) U.S. Cl.
CPC ............. *A61B 5/037* (2013.01); *A61B 5/1076* (2013.01); *A61B 5/205* (2013.01); *A61B 5/4211* (2013.01); *A61B 5/4233* (2013.01); *A61B 5/6853* (2013.01); *A61M 39/22* (2013.01)

(56) References Cited

U.S. PATENT DOCUMENTS

| | | | |
|---|---|---|---|
| 4,809,710 | A | 3/1989 | Williamson |
| 5,674,798 | A | 10/1997 | Kitamura et al. |
| 5,865,801 | A | 2/1999 | Houser |
| 5,924,984 | A | 7/1999 | Rao |
| 5,951,497 | A | 9/1999 | Wallace et al. |
| 5,984,879 | A | 11/1999 | Wallace et al. |
| 6,029,076 | A | 2/2000 | Fiddian-Greene et al. |
| 6,059,740 | A | 5/2000 | Leivseth et al. |
| 6,083,205 | A * | 7/2000 | Bourne et al. ............... 604/246 |
| 6,117,086 | A | 9/2000 | Shulze |
| 6,117,091 | A | 9/2000 | Young et al. |
| 6,119,697 | A | 9/2000 | Engel et al. |
| 6,231,524 | B1 | 5/2001 | Wallace et al. |
| 6,254,598 | B1 | 7/2001 | Edwards et al. |
| 6,447,462 | B1 | 9/2002 | Wallace et al. |
| 6,468,232 | B1 | 10/2002 | Ashton-Miller et al. |
| 6,773,452 | B2 | 8/2004 | Shaker |
| 6,974,422 | B1 | 12/2005 | Millar |
| 6,997,884 | B2 | 2/2006 | Ulmsten et al. |
| 7,004,899 | B2 | 2/2006 | Tracey |
| 7,056,319 | B2 | 6/2006 | Aliperti et al. |
| 7,381,190 | B2 | 6/2008 | Sugrue et al. |
| 7,637,876 | B2 | 12/2009 | Schlumpf |
| 2010/0094328 | A1 | 4/2010 | O'Dea et al. |
| 2010/0167801 | A1* | 7/2010 | Karkanias et al. ............... 463/7 |

OTHER PUBLICATIONS

Fox et al. "Effect of Aging on Anorectal and Pelvic Floor Functions in Females". Dis Colon Rectum. Nov. 2006. 49: 1-10.

Noelting et al. "Normal Values for High-Resolution Anorectal Manometry in Healthy Women: Effects of Age and Significance of Rectoanal Gradient". American Journal of Gastroenterology. 2012. pp. 1-25.

Rao et al. "Minimum Standards of Anorectal Manometry". Neurogastroenterol. Mot. 2002. 14: 553-559.

Geibel et al., "Treatment Strategies in Obstructed Defecation and Fecal Incontinence", World Journal of Gastroenterology, May 28, 2006, pp. 3168-3173.

Zbar, "Compliance and Capacity of the Normal Human Rectum—Physical Considerations and Measurement Pitfalls", Acta Chir Iugosl, vol. 54(2), 2007, pp. 49-57.

\* cited by examiner

Figure 7

Required Valve Positions (O=Open, X=Closed, blank=either)

| Step | Action | Description | Transducer Valves | Inter-Plenum Valves | Syringe Valve |
|------|--------|-------------|:-:|:-:|:-:|
| 1 | Open all transducers and all balloons to the plenum to equilibrate | Equalize @ atm pressure | O | O | X |
| 2 | Close off transducer valves | Sampling for normalization of readings at low pressure | X | | |
| 3 | Read low pressure values from transducers | | X | | |
| 4 | Open all transducers and all balloons to the plenum | Equalize | O | O | X |
| 5 | Pressurize the balloons with ~4cc air | Equalize | O | O | O |
| 6 | Close off transducer valves | | X | | X |
| 7 | Read high pressure from transducers | Sampling for normalization of readings at high pressure | X | | X |
| 8 | Priming is complete | | X | | X |
| 9 | Go to operation mode. Balloons remain inflated | Data collection | O | X | X |

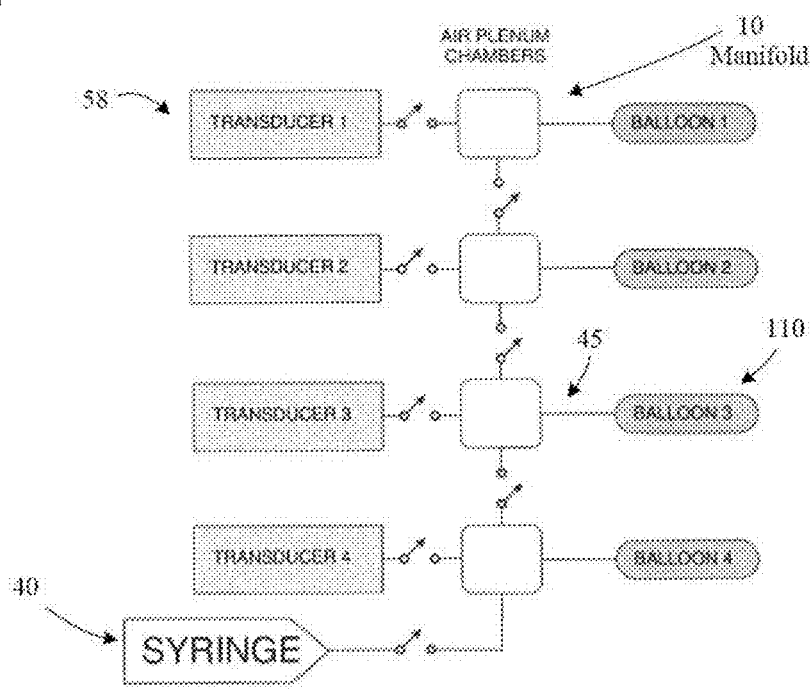

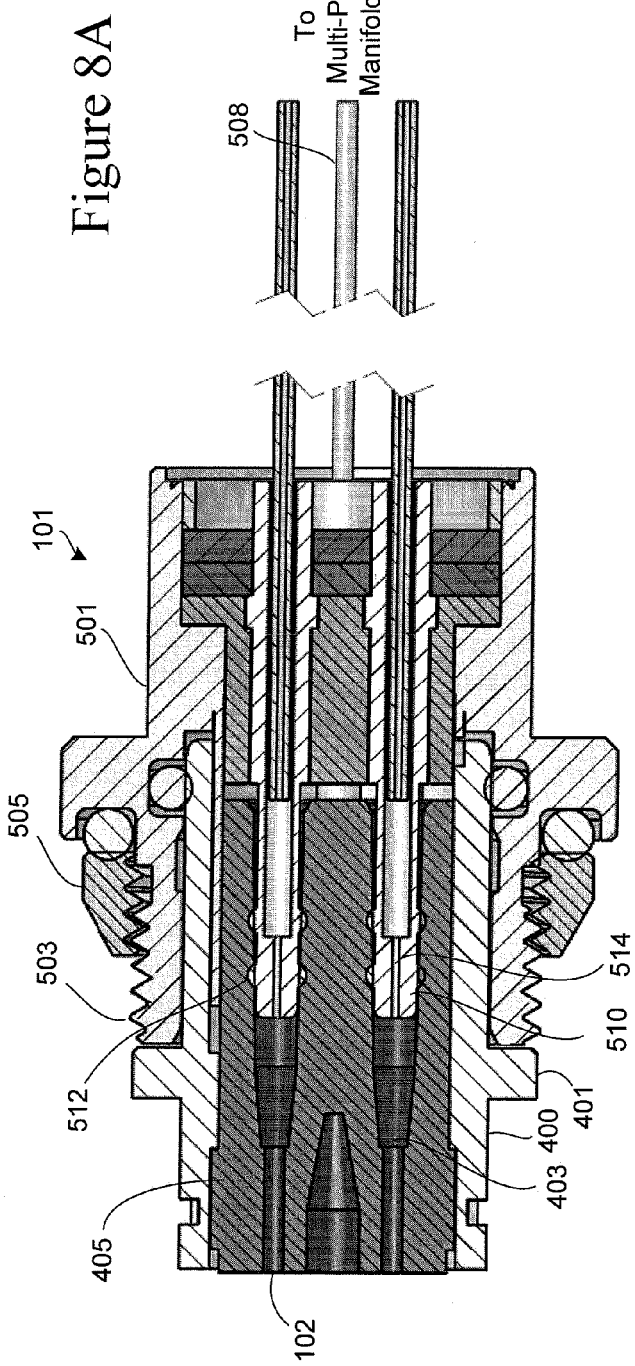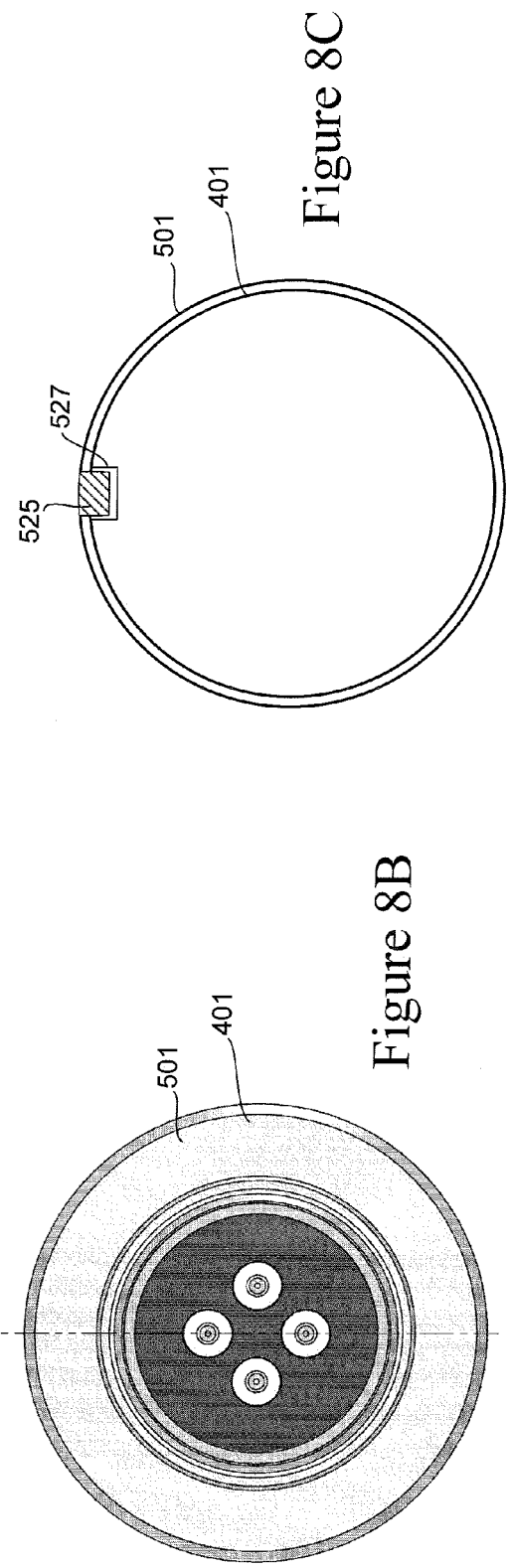
Figure 8A
Figure 8B
Figure 8C

Figure 14

MOTILITY MANOMETER PRIMING MANIFOLD SYSTEM WITH ICON-BASED USER INTERFACE AND WIRELESS CONNECTIVITY

RELATED PATENT DOCUMENTS

This application claims the benefit of Provisional Patent Application Ser. Nos. 61/588,163 and 61/588,168 both filed on Jan. 18, 2012, to which priority is claimed pursuant to 35 U.S.C. §119(e) and which are hereby incorporated herein by reference.

SUMMARY

Various embodiments are directed to apparatuses and methods for selectively coupling and decoupling fluidic pathways between a multiplicity of components of a pressurizable fluidic system. Embodiments are directed to a multi-mode manifold arrangement for selectively coupling and decoupling fluid connections between a multiplicity of components of a pressurizable fluidic system. Embodiments are directed to a multi-mode manifold arrangement for selectively coupling and decoupling fluid connections between a multiplicity of components of a pressurizable fluidic system that requires charging for proper operation.

Other embodiments are directed to pressure sensing devices that incorporate an apparatus for selectively coupling and decoupling fluidic pathways between a multiplicity of device components. Embodiments are directed to pressure sensing devices that incorporate a multi-mode manifold arrangement for selectively coupling and decoupling fluid connections between a multiplicity of device components. Embodiments are directed to apparatuses and methods for effecting selective fluidic coupling and decoupling between charging, pressure sensing, and motility measurement lumen components of a pressure sensing device that requires charging for proper operation.

Further embodiments are directed to apparatuses and methods for selectively coupling and decoupling fluid pathways between a multiplicity of components of a motility manometer that requires priming for proper operation. Embodiments are directed to a motility manometer for measuring pressure changes in a body cavity which incorporates a multi-mode manifold arrangement for selectively coupling and decoupling fluid connections between charging, pressure sensing, and motility measurement lumen components of a hand-held motility manometer.

Some embodiments are directed to a pressure sensing catheter comprising a motility measurement balloon arrangement. In some embodiments, the motility measurement balloon arrangement includes a multiplicity of motility measurement balloons. In other embodiments, a single motility measurement balloon is employed. The catheter includes a pneumatic connector configured to mechanically and pneumatically connect to a corresponding pneumatic connector provided on a housing of a pressure sensing device or FOB (frequency operated button). In embodiments that employ a multiplicity of motility measurement balloons, the catheter's pneumatic connector incorporates a corresponding number of female connectors each having a fluid channel that fluidly couples with a balloon lumen of the catheter (or receives a terminus of a balloon lumen). The female connectors are configured to matingly couple with corresponding pins (male) of the housing's pneumatic connector. Each pin includes a fluid channel that is configured to fluidly couple to a corresponding female connector. In some embodiments, the catheter's pneumatic connector is keyed to ensure proper alignment between the female fluid connectors and corresponding fluid pins of the housing's pneumatic connector when secured thereto. In some embodiments, the catheter's pneumatic connector includes one or more male pins with fluid channels, while the pneumatic connector of the FOB housing includes the female fluid connectors.

Various embodiments are directed to a pressure sensing device or FOB comprising a multi-mode manifold and a plurality of pressure transducers. The manifold is fluidly coupled to a pneumatic housing connector, a priming port, and the pressure transducers. The pneumatic housing connector is configured to mechanically and fluidly couple to a single- or multiple-channel connector of a pressure sensing catheter. The manifold is configured to provide selective coupling and decoupling between the pneumatic housing connector, the priming port, and the pressure transducers. In some embodiments, the pressure sensing device is configured to calibrate the pressure transducers at atmospheric pressure and initiate pressure measurements with both the pressure transducers and the one or more motility measurement balloons of the pressure sensing catheter at atmospheric pressure. The pressure sensing device can incorporate a single or multi-port pneumatic connector of a type described herein. According to various embodiments, the pressure sensing device is incorporated in a hand-held housing which includes a port selector coupled to the manifold, a display, and a battery or other power source. In some embodiments, the pressure sensing device further includes a distension balloon pressure transducer which is fluidly coupled to a distension balloon connector on the housing. The distension balloon connector is configured to fluidly couple to a distension balloon lumen and distension balloon of a pressure sensing catheter. The distension balloon can be implemented as a compliant or semi-compliant balloon, which allows for cavity compliance testing (e.g., rectal compliance testing).

According to some embodiments, a system includes a catheter comprising a distal distension balloon and a plurality of circumferentially arranged motility measurement balloons proximal of the distension balloon. A manifold includes a plurality of balloon ports each configured to fluidly couple to one of the motility measurement balloons, a plurality of pressure transducer ports, and a priming port. A port selector is coupled to the manifold and movable between different positions. Each of the different port selector positions causes the manifold to establish different fluidic couplings between the respective motility balloon, pressure transducer, and priming ports. A pressure sensing device comprises a plurality of pressure transducers each fluidly coupled to one of the plurality of pressure transducer ports. The pressure sensing device is configured to coordinate calibration of the pressure transducers at atmospheric pressure with the port selector in a first position and motility balloon pressure measurements with the port selector in a third. The pressure sensing device is further configured to coordinate priming of the motility measurement balloons with the port selector is in a second position.

In accordance with other embodiments, a system includes an anorectal manometry catheter having a distal distension balloon comprising a compliant or semi-compliant balloon, and a single or a plurality of circumferentially arranged motility measurement balloons proximal of the distension balloon. A manifold comprises a single or a plurality of balloon ports each configured to fluidly couple to one of the motility measurement balloons, a single or a plurality of pressure transducer ports, and a priming port. A pressure sensing device comprises a rectal pressure transducer fluidly coupled to the distension balloon, and a single or a plurality of pressure transducers each fluidly coupled to the single or plurality of pressure transducer ports. The pressure sensing device is configured to coordinate calibration of the single or plurality of pressure transducers at atmospheric pressure with the manifold in a first position, and coordinate rectal compliance measurements using the rectal pressure transducer and motility balloon pressure measurements using the single or plurality of pressure transducers with the manifold in a third position. The pressure sensing device is further configured to coordinate priming of the motility measurement balloons with the manifold in a second position.

According to further embodiments, a method involves selectively establishing different fluidic couplings between a distal distension balloon and a plurality of circumferentially arranged motility measurement balloons of a manometry catheter, a plurality of pressure transducers, and a priming port of a multi-mode manifold in accordance with different orientations of the manifold fluidly coupled thereto. The method also involves calibrating the pressure transducers at atmospheric pressure and charging the motility measurement balloons so as to inflate the motility measurement balloons. After charging the motility measurement balloons, the method involves exposing the motility measurement balloons to atmospheric pressure. The method further involves operating the motility measurement balloons to perform motility measurements.

These and other features can be understood in view of the following detailed discussion and the accompanying drawings.

BRIEF DESCRIPTION OF THE DRAWINGS

FIG. 7 shows various valve positions required to perform the different actions illustrated in the table of FIG. 7 in accordance with various embodiments;

FIGS. 8A-8C illustrate a multi-port pneumatic connector system in accordance with various embodiments;

FIGS. 11-20 are graphical diagrams showing an icon-based user interface for a hand-held motility manometer in accordance with various embodiments of the disclosure.

DETAILED DESCRIPTION

According to various embodiments, a multi-mode manifold arrangement is incorporated in a motility pressure measuring device for selectively coupling and decoupling fluid connections between charging, pressure sensing, and motility measurement lumen components of the device. Embodiments are directed to measuring pressure changes in a cavity of the body using a pressure measuring device that incorporates a multi-mode manifold arrangement for selectively coupling and decoupling fluid connections between charging, pressure sensing, and motility measurement lumen arrangements of the device. According to various embodiments, pressure measuring devices, such as manometers, can be configured for performing different types of manometry, including esophageal, anorectal, urinary, and uteral manometry, among others.

Esophageal manometry is a test that measures functioning of the lower section of the esophagus. Esophageal manometry evaluates the lower esophageal sphincter valve that prevents stomach acids from refluxing into the esophagus. Esophageal manometry aids a clinician in determining whether a patient's esophagus can properly move food into the stomach.

Anorectal manometry is a test performed to evaluate patients with constipation or fecal incontinence. More specifically, anorectal manometry is a test that measures the pressures of the anal sphincter muscles, the sensation in the rectum, and the neural reflexes that are needed for normal bowel movements. According to various testing approaches, a catheter in the form of a small, short, and somewhat narrow blunt tube is gently inserted into the rectum. The catheter contains a balloon-like device at a location where it will come into contact with the anal sphincter. The catheter is connected to a device that measures pressure (and pressure changes) during the test.

During the test, the small balloon is slightly inflated in the rectum to assess the normal reflex pathways. The patient may be asked to squeeze, relax, and sometimes push at various times. Anal sphincter muscle pressures are measured during each of these maneuvers. Anal manometry measures how strong the sphincter muscles are and whether they relax as they should during voiding. Anal manometry provides useful helpful information to the clinician in treating patients with pelvic floor weakness, pelvic floor spasm, fecal incontinence or severe constipation. Based on the results of this test, and of surface (transcutaneous) EMG of the pelvic floor muscle if performed, the clinician prescribes a therapy, typically in the form of an individualized exercise prescription, but sometimes medications as well, and often neuromodulation.

Figure 1:
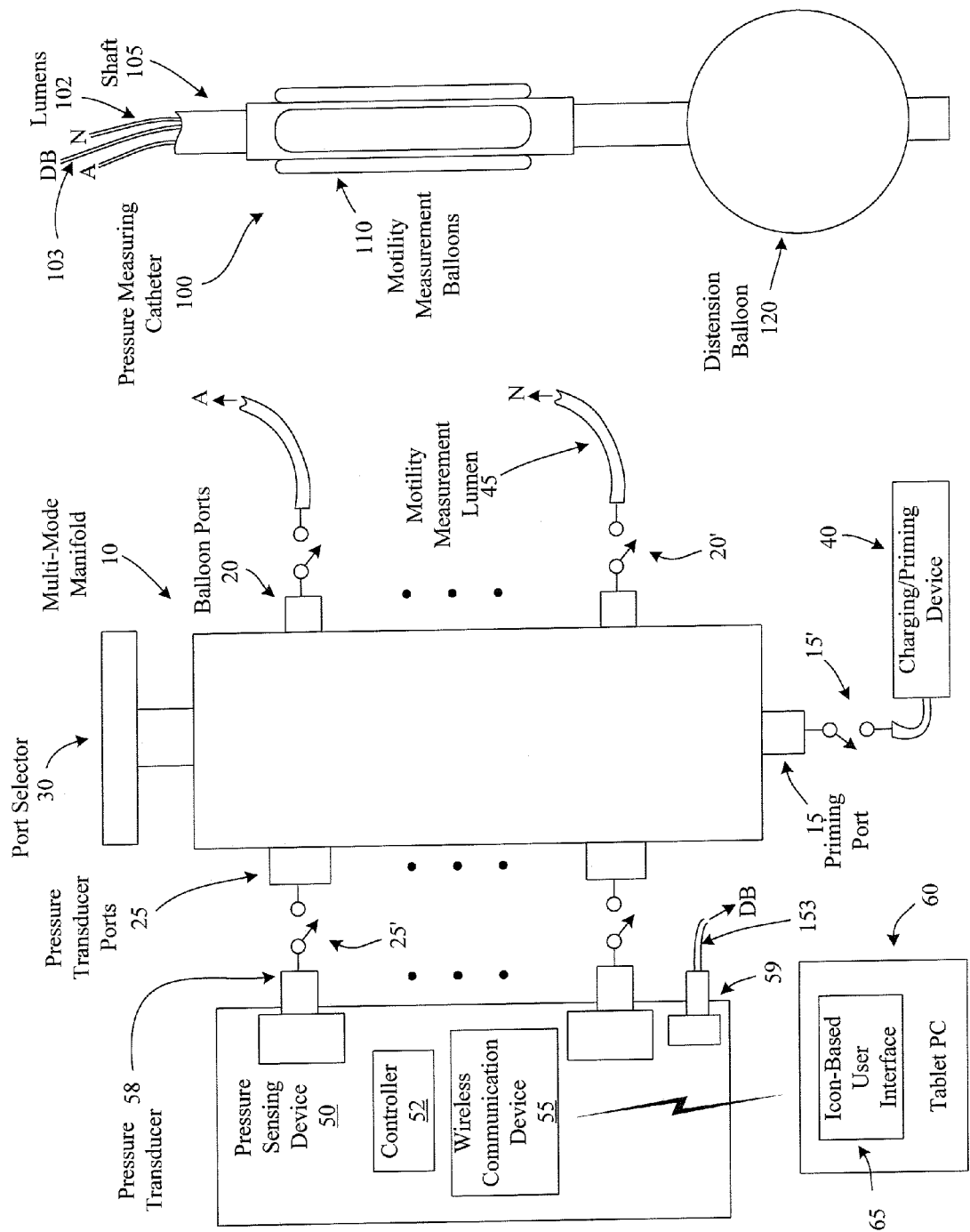
FIG. 1 is a block diagram of pressure sensing system which includes a multi-mode manifold and a pressure sensing device in accordance with various embodiments.

Turning now to FIG. 1, there is shown a block diagram of a pressure sensing system which includes a multi-mode manifold 10 and a pressure sensing device 50 in accordance with various embodiments. The following discussion describes the multi-mode manifold 10 in the context of a pressure sensing device implemented as a motility manometer configured for sensing pressure changes in a body cavity (e.g., esophagus, anal-rectal region, colon, urinary, uterus). It is understood that the multi-mode manifold 10 and other components of the system shown in the figures of the disclosure can be incorporated in other pressurizable fluidic systems, including apparatuses other than pressure sensing devices or systems.

The multi-mode manifold 10 and pressure sensing device 50, along with other components such as a power source, are housed in a hand-held or portable chassis. For example, a hand-held motility manometer is configured to incorporate the multi-mode manifold 10 and pressure sensing device 50 shown in FIG. 1, although other system configurations are contemplated. The multi-mode manifold 10 includes a number of ports, including a multiplicity of balloon ports 20, a multiplicity of pressure transducer ports 25, and a priming port 15. Different fluidic interconnections between the various ports are achieved by moving a port selector 30, which can be moved to different positions for selectively coupling and decoupling various fluidic pathways through the multi-mode manifold 10. In some embodiments, the port selector 30 is manually moved to desired positions to effectuate different fluidic couplings between the balloon ports 20, the pressure transducer ports 25, and the priming port 15. In other embodiments, an electric motor can be controlled to move the manifold 10 so as to make the desired fluidic interconnections.

Each of the pressure transducer ports 25 of the multi-mode manifold 10 is configured to fluidly couple to one of a multiplicity of pressure transducers 58 provided on the pressure sensing device 50. The pressure sensing device 50 includes a number of components, including a controller 52 and a wireless communication device 55, among other components. According to some embodiments, the wireless communication device 55 of the pressure sensing device 50 is configured to wirelessly communicate with an external device or system, such as a tablet PC 60. The tablet PC is configured to execute software for interfacing with and controlling the pressure sensing system. The tablet PC 60 may be configured with a touch sensitive screen that allows for touch driven clinician interaction with the pressure sensing system via an icon-based user interface 65. According to alternative embodiments, the pressure sensing device 50 can include a wired communication interface rather than a wireless communication device 55. A wireless communication device 55 affords the opportunity to eliminate all wires and cables between the tablet PC 60 or other processing device and a manometer that incorporates the multi-mode manifold 10 and pressure sensing device 50. The tablet PC 60 preferably includes an icon-based user interface 65.

Incorporating a wireless communication device 55 into a hand held manometer allows motility measurements to be transmitted wirelessly to a separate system or device, such as tablet PC 60. A motility manometer that incorporates a wireless communication device 55 eliminates the need for cables used in traditional manometry systems. This eliminates the need for bulky cables that can cause issues during use near and around patients, and isolates the patient from any potential electrical hazard. Readings taken by the pressure transducers 58 can be transmitted wirelessly to a tablet PC 60 loaded with motility software. Various communication protocols can be implemented by the wireless communication device 55, such as MICS, ISM, RF Wireless protocols (WiFiMax, IEEE 802.11a/b/g/n, etc.), BLUETOOTH® (high or low power methods), and ZIG-BEE® or similar specification, such as those based on the IEEE 802.15.4 standard, or other public or proprietary wireless protocol.

Each of the balloon ports 20 of the multi-mode manifold 10 is configured to fluidly coupled to one of a multiplicity of motility measurement lumens 45, represented by lumens A through N in FIG. 1. Each of the motility measurement lumens 45 is fluidly coupled to one of a multiplicity of pressurizable lumens 102 of a pressure measuring catheter 100. According to various embodiments, the pressure measuring catheter 100 includes a shaft 105 having a distal end that supports two balloon arrangements. In the embodiment of the pressure measuring catheter 100 shown in FIG. 1, a distension balloon 120 is mounted at a distal end of the shaft 105, and a motility measurement balloon arrangement 110 is mounted proximal of the distension balloon 120. The motility measurement balloon arrangement 110 includes either a single or a multiplicity of balloons, such as four such balloons (e.g., 4-6 balloons). Each of the motility measurement balloons 110 is fluidly coupled to one of the shaft lumens 102 and one of the motility measurement lumens 45.

The lumen arrangement of the shaft 105 also includes a distal balloon lumen 103, labeled lumen DB, which is fluidly coupled to the distal balloon 120. The distal balloon lumen 103 is fluidly coupled to a pressure transducer 59 of the pressure sensing device 50. The fluid connection between the distal balloon lumen 103 and the pressure transducer 59 can be routed through the multi-mode manifold 10 or can bypass the manifold 10. For example, and according to some embodiments, the distal balloon lumen 103 is fluidly coupled to a stopcock luer connector located towards a proximal end of the catheter 100, and an extension tube 153 is provided to fluidly couple the distal balloon lumen 103 to the pressure transducer 59 via a luer connector. In some embodiments, the distension balloon 120 is configured as a compliant or semi-compliant balloon, and therefore retains is round or elliptical shape when inflated. Use of a compliant or semi-compliant distension balloon 120 provides for testing of rectal compliance in additional to anorectal manometry measurements.

The fluid connections between the motility measurement lumens 45 and corresponding balloon ports 20 provide for establishing independent fluid channels between each of the motility measurement balloons 110 of the pressure measuring catheter 100 and the multi-mode manifold 10. Fluidly coupling each of the pressure transducer ports 25 of the multi-mode manifold 10 to a corresponding pressure transducer 58 of the pressure sensing device 50 provides independent fluid channels between each of the motility measurement balloons 110 of the pressure measuring catheter 100 and individual pressure transducers 58 of the pressure sensing device 50.

Figures 2A, 2B:
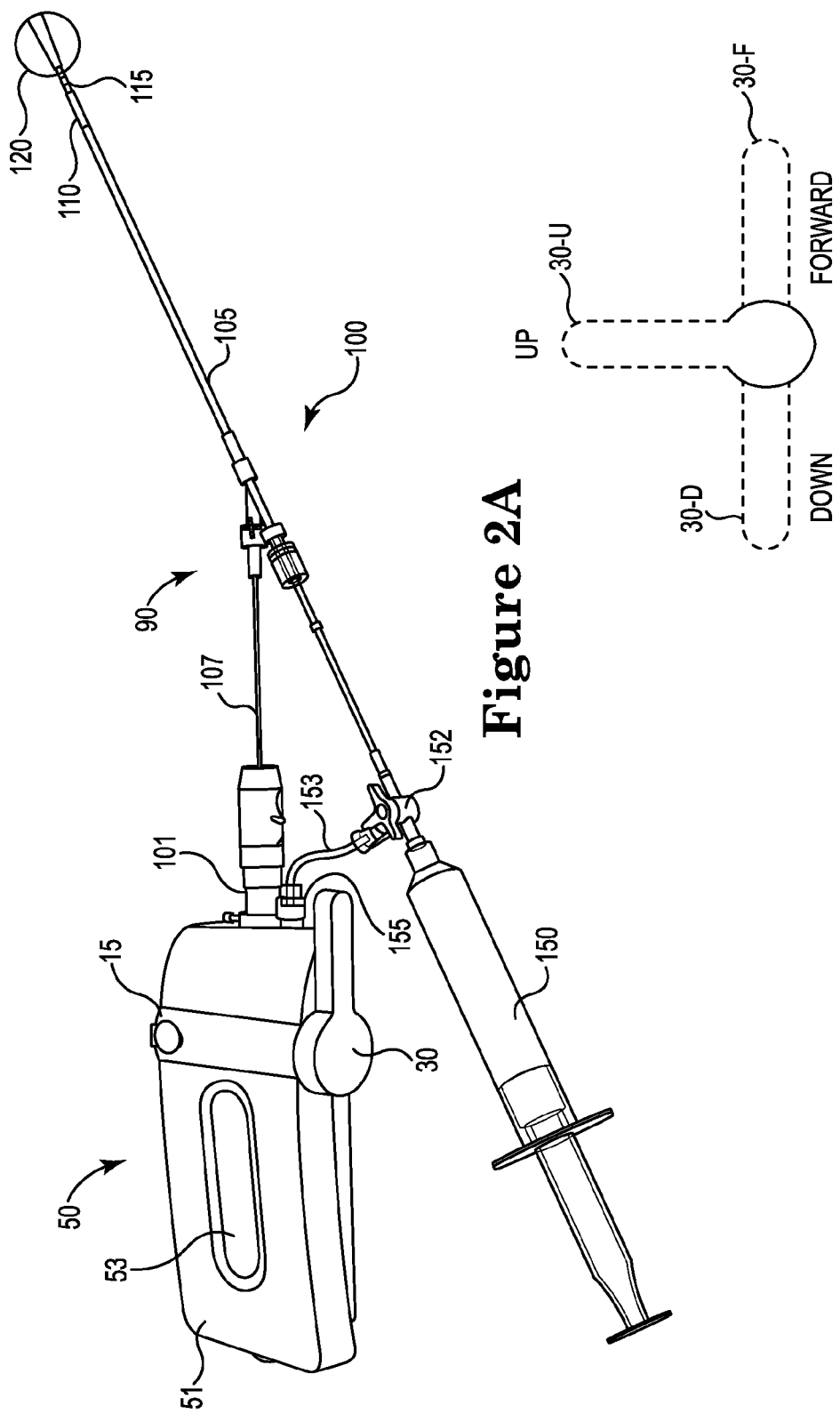
FIG. 2A illustrates an embodiment of a pressure sensing system in accordance with various embodiments.
FIG. 2B illustrates the port selector shown in FIG. 2A in different positions that provide for different functionality in accordance with various embodiments.

FIG. 2A illustrates an embodiment of a pressure sensing system in accordance with various embodiments. In some embodiments, the pressure sensing system 90 shown in FIG. 2A is implemented as a hand-held, portable anorectal manometry system. In some implementations, the catheter section 100 of the pressure sensing system 90 is manufactured as a disposable product, while the pressure sensing device 50 is a reusable product. The catheter 100 of the pressure sensing system 90 illustrated in FIG. 2A includes a shaft 105 which supports a distal distension balloon 120 and motility measurement balloons 110 circumferentially arranged about the shaft 105. A series of depth indicators 115 is provided on the shaft 105 between the distension balloon 120 and the motility measurement balloons 110. The depth indicators 115 are separated from one another by a predetermined distance, such as 1 cm. The depth indicators 115 allow the clinician to know how deep into a body cavity the distal end of the catheter 100 has been inserted.

The number of, and spacing between, the depth indicators 115 varies depending on the type of catheter being used and the body cavity being examined. In the case of an anorectal manometry catheter embodiment, for example, between about 4 and 10 (e.g., 6) depth indicators 115 spaced 1 cm apart is generally appropriate. In addition, an orientation indicator (not shown), such as "P" for posterior, can be provided on the shaft 105 to indicate the rotational orientation of the catheter. This is important in some embodiments where different regions of anatomy are being tested using discrete motility measurement balloons 110. For example, anorectal motility measurements can be obtained using four motility measurement balloons 110 mounted on the shaft at 0°, 90°, 180°, and 270° locations about the circumference of the shaft 105. The four balloons 110 at these locations are identified as posterior (P), anterior (A), left (L), and right (R) balloons, with the posterior (P) balloon referring to the balloon that is oriented to face the patient's spine. By properly aligning the orientation indicator (e.g., "P") on the catheter shaft 105 with respect to a specified body reference point (e.g., the spine), the pressure measurements made using the 4 balloons accurately correspond to posterior, anterior, left, and right regions of the anal canal.

According to other embodiments, motility measurements (e.g., anorectal motility measurements) can be obtained using a catheter having a single measurement balloon mounted circumferentially about the shaft 105. In configurations that employ a single motility measurement balloon, a single channel of pressure data is obtained, which may be sufficient in many applications. In some embodiments, the single balloon may extend partially around the circumference of the catheter's shaft 105, such as an arc of 90°, 180°, or 270° for example.

It is noted that the typical length of the human anal canal ranges between about 20-45 mm. In various embodiments, the length of the motility measurement balloons 110 is about 20 mm. The relationship of the length of the motility measurement balloons 110 relative to the average length of a patient's anal cavity allows for viable anorectal manometry testing to be conducted using a single site without need for repositioning for a large majority of patients. At most, only two testing sites would be needed, thus requiring only a single repositioning event for a small percentage of patients having a longer than average anal canal (such patients constitute only about 15-20% of the population). Conventional anorectal manometry catheters typically employ relatively short motility measurement balloons, requiring a multiplicity of tests to be performed at a multiplicity of anal canal depths, resulting in additional time and costs.

FIG. 2A further shows a charging syringe 150 fluidly coupled to the distension balloon 120. The charging syringe 150 is used to pressurize the distension balloon 120 during use. In some embodiments, the distension balloon 120 requires a minimal charge (e.g., 10 cc) to ensure proper operation. This minimal charge only partially inflates the distension balloon 120. In some embodiments, the distension balloon 120 has a length of about 55 mm, a diameter of about 30 mm, and can hold a maximum safe pressure of about 180 cc. The pressure within the distension balloon 120 can be measured using a distension balloon (DB) pressure transducer (transducer 59 shown in FIG. 1) of the pressure sensing device 50, which can be fluidly coupled to the distension balloon lumen in the catheter shaft via an extension tube 153 connected between a single luer connector 155 and a stopcock luer connector 152. The stopcock luer connector 152 allows selective fluidic coupling and decoupling between the charging syringe 150, the distension balloon 120, and the distension balloon pressure transducer 59 via the extension tube 153. As previously discussed, the distension balloon 120 according to some embodiments is implemented as a compliant or semi-compliant balloon, allowing for rectal compliance testing. Conventional anorectal manometry catheters typically employ a compliant distension balloon that expands into the rectal cavity during inflation, rendering the distension balloon unusable for rectal compliance testing.

The pressure sensing device 50 includes a hand-held housing 51 within which a number of the aforementioned components are housed, including the multi-mode manifold 10, pressure sensing device electronics (e.g., controller 52, wireless communication device 55, pressure transducers 58 and 59), power supply (e.g., battery), and fluidic ports 15, 20, 25, and lumens 45. The housing 51 also supports a display 53, a priming port 15 (with detachable cover shown), a port selector lever 30, a multi-port connector 101, and a luer connector 155. It is noted that the pressure sensing device 50 in the housing 51 shown in FIG. 2A is also referred to as an FOB (frequency operated button).

The charging or priming port 15 is configured to receive a syringe or other charging device that contains a charged fluid (e.g., air). The priming port 15 can also be used to expose the multi-mode manifold and various fluidic couplings within the pressure sensing device 50 to atmospheric pressure, assuming the syringe is not positioned within the priming port 15. The priming port 15 can be fluidly coupled to the motility measurement balloons 110 via the multi-mode manifold for charging with a pressurized fluid (e.g., 3 or 4 cc of air) or exposed to air at atmospheric pressure. The priming port 15, when open, can also provide a conduit to atmosphere for the pressure transducers 58. The display 53 includes a number of different indicators and buttons. According to some embodiments, the display 53 includes a power button, a system on/off indicator (e.g., green=on), a battery status indicator, and a wireless connection button/status indicator (e.g., BLUETOOTH® icon). It is understood that other indicators and buttons can be provided to provide other functionality and information.

FIG. 2A further shows a port selector 30 in the form of a lever mounted on the side of the housing 51. The port selector 30 is coupled to the multi-mode manifold 10 and controls the movement (e.g., rotation) of the multi-mode manifold 10, which effectuates predefined fluidic couplings between the four motility measurement balloon ports 20, the four pressure transducer ports 25, and the priming/charging port 15, as shown in FIG. 1. Selected fluidic connections between these ports are coupled and decoupled depending on the position of the multi-mode manifold 10 as controlled by the port selector 30. These fluid connections are also referred to herein as valves, and as such there are four balloon port valves 20', four pressure transducer valves 25', and a priming port valve 15' (see FIG. 1).

As is best seen in FIG. 2B, and according to various embodiments, the port selector 30 has three main positions (e.g., forward, up, and down) that provide for different functionality. Intermediate port selector positions between these three main positions can provide additional functionality. It is noted that the port selector 30 shown in FIG. 2A is in the forward position.

In the down position 30-D (also referred to herein as the first position) shown in FIG. 2B, and with reference also to FIG. 1, all of the balloon port valves 20', the pressure transducer valves 25', and the priming port valve 15' are open to atmosphere. With the port selector 30 in the down 30-D, the motility measurement balloons 110, the pressure transducers 58, and the priming port 15 equalize to atmospheric pressure. When the port selector 30 is in the down position 30-D, the pressure transducers 58 can be calibrated at atmospheric pressure with the priming port 15 open to atmosphere (i.e., charging syringe and valve cap removed from the priming port 15).

With the port selector 30 in the up position 30-U (also referred to herein as the second position), the pressure transducer valves 25' are closed to atmosphere and are also closed to the balloon port valves 20' and the priming port valve 15'. The priming port valve 15' is open, which can be to atmosphere or a charging syringe situated on/in the priming port 15. The balloon port valves 20' are open to the priming port valve 15'. When the port selector 30 is in the up position 30-U, the motility measurement balloons 110 can be charged using a syringe place within the priming port 15.

When the port selector 30 is moved to a position between the up position 30-U and the forward position 30-F (also referred to herein as the third position), the pressure transducer valves 25' are closed and isolated. Lastly, when the port selector 30 is in the forward position 30-F, the pressure transducer valves 25' are open, the balloon port valves 20' are open, and the priming port valve 15' is closed. In the forward position 30-F, the pressure transducers 58 are fluidly coupled to the motility measurement balloons 110, and the system is ready for operation.

FIGS. 3-6 illustrate how moving the port selector 30 to different positions allows the clinician to selectively couple and decouple various fluidic pathways between the pressure transducer ports 25, balloon ports 20, and priming port 15 via the multi-mode manifold 10. FIGS. 3-6 also show an electronics board 51 of the pressure sensing device 50 which supports various electric and electronic components, including the pressure transducers 58. Not shown on the electronics board 51 is a pressure transducer 59 dedicated to measuring pressure within the distension balloon 120, as shown in FIG. 1. These and other components are coupled to a controller 52 also mounted on the electronics board 51.

Manometers need to be primed prior to use. The priming process initializes the complete motility measurement system prior to use. The multi-mode manifold 10 shown in FIGS. 3-6 is capable of being incorporated into a hand-held manometer, allowing the charging of the motility measurement lumens while disconnected from the manometer pressure transducers 58. According to various embodiments, the multi-mode manifold 10 allows decoupling of manometer pressure transducers 58 from the system prior to charging the motility measurement lumens 110.

Figure 3:
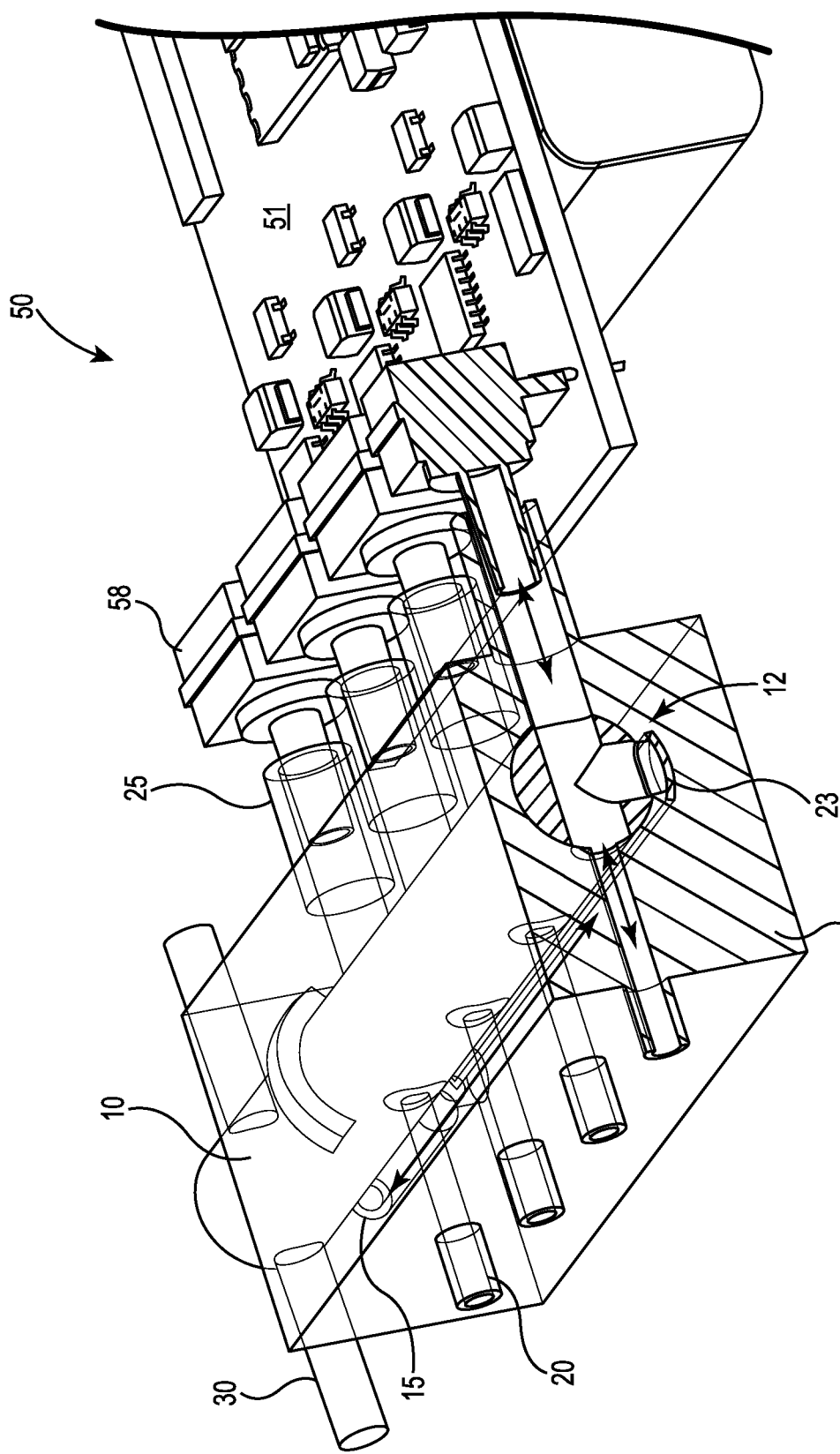
FIG. 3 shows fluidic interconnections between the ports of a multi-mode manifold when the port selector is in a first position for equalizing pressure within the system to atmospheric pressure in accordance with various embodiments.

FIG. 3 shows various features of the multi-mode manifold 10, including the priming port 15, the pressure transducer ports 25, and the balloon ports 20. FIG. 3 also shows internal features of the multi-mode manifold 10, including fluidic connections that can be made between the priming port 15, the pressure transducer ports 25, the balloon ports 20, and a connecting chamber 23 between these ports. A central longitudinal bore 12 provided in a manifold block 11 is fluidly connected to each of the ports 15, 20, and 25. Selective coupling and decoupling of the various ports 15, 20, and 25 is achieve by use of a port selector 30 configured to be received by the central longitudinal bore 12, as is shown in FIG. 3.

FIG. 3 shows the fluidic interconnections between the ports 15, 20, and 25 when the port selector 30 is in a first position, which corresponds to the down 30-D position of the port selector 30 shown in FIG. 2B. It is understood that the port selector 30 may have a configuration different from that shown in FIG. 3 and other figures for making different fluidic interconnections between the ports 15, 20, and 25 depending on desired functionality. With the port selector 30 in the down position 30-D, all ports 15, 20, and 25 are open to atmosphere via the priming port 15. This orientation of the multi-mode manifold 10 allows the system to equalize at atmospheric pressure, and further allows initial atmospheric readings to be taken by the pressure transducers 58 independent of the motility measurement lumens 45. The pressure transducers 58 are zeroed out at atmospheric pressure by the controller 52 as part of the calibration procedure.

Figure 4:
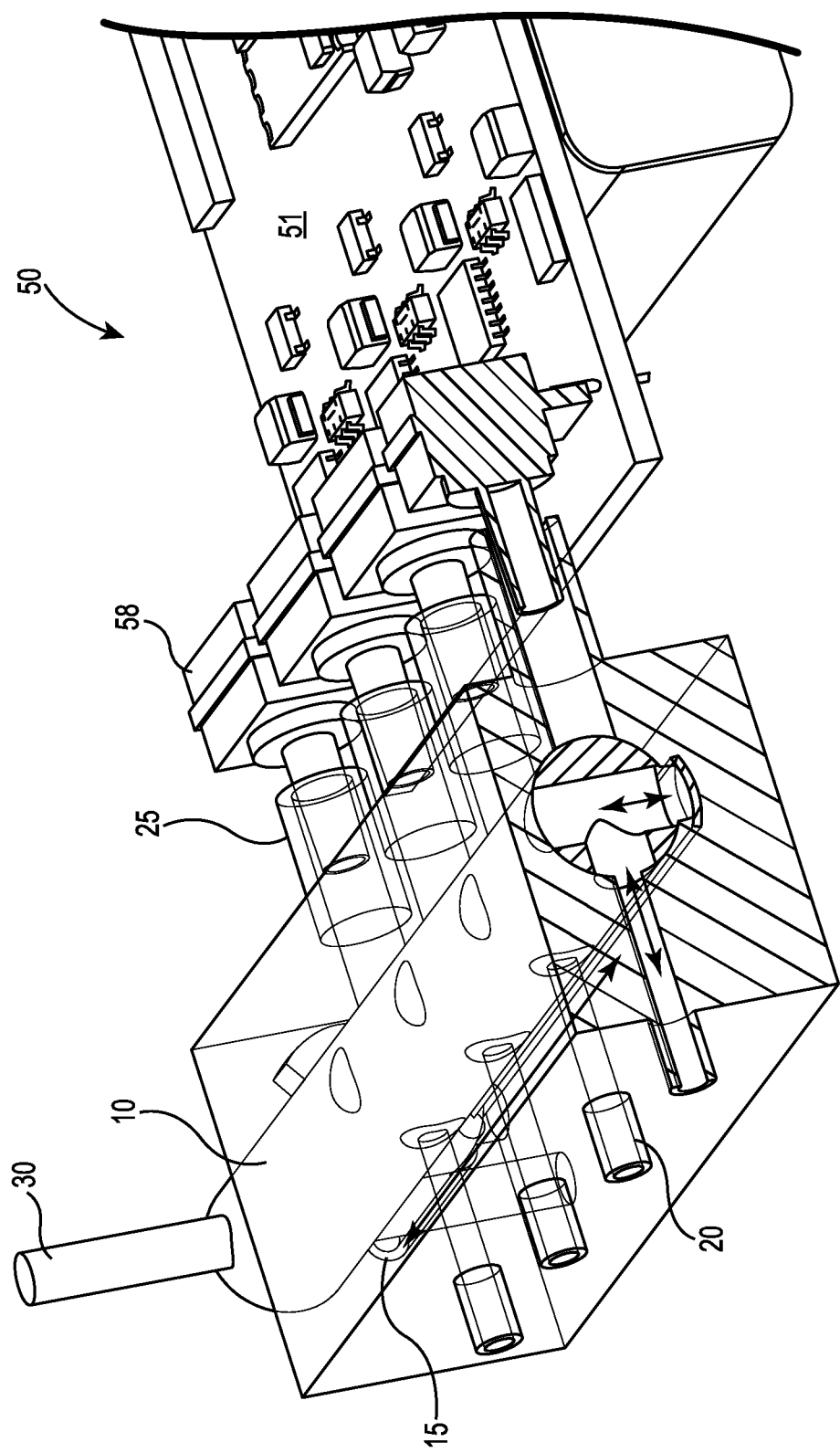
FIG. 4 shows fluidic interconnections between the ports of a multi-mode manifold when the port selector is in a second position for priming motility measurement balloons of the system in accordance with various embodiments.

FIG. 4 shows the port selector 30 in the up 30-U position shown in FIG. 2B. In the up 30-U position, the balloon ports 20 are connected to the priming port 15 (and may also be connected to each other). The up 30-U position causes the multi-mode manifold 10 to fluidly couple only the motility measurement lumens 45 and the priming port 15, and keeps the pressure transducers 58 isolated. During the priming procedure, a charging syringe is fluidly connected to the priming port 15, typically with 3 or 4 cc of air, to charge the motility measurement balloons 110.

According to some embodiments, prior to completion of the priming procedure, a pressure transducer calibration procedure is performed at atmospheric pressure, rather than at a charged pressure. It has been found by the inventor that calibrating the pressure transducers 58 at atmospheric pressure and then initiating pressure measurements with both the pressure transducers 58 and the motility measurement balloons 110 at atmospheric pressure provides for a substantial increase in pressure measurement accuracy. It was found that after charging the motility measurement balloons 110 and then returning the balloons 110 to atmospheric pressure, the balloon 110 substantially retained their inflated volume. During the calibration procedure, the charging syringe is removed from the priming port 15 opening the motility measurement balloons 110 to atmosphere, and then the port selector 30 is moved to the forward 30-F position, thereby connecting the calibrated transducer ports 25 to the calibrated motility measurement balloons 110. Both the pressure transducers 58 and motility measurement balloons 110 are at atmospheric pressure which completes the calibration procedure.

Figure 5:
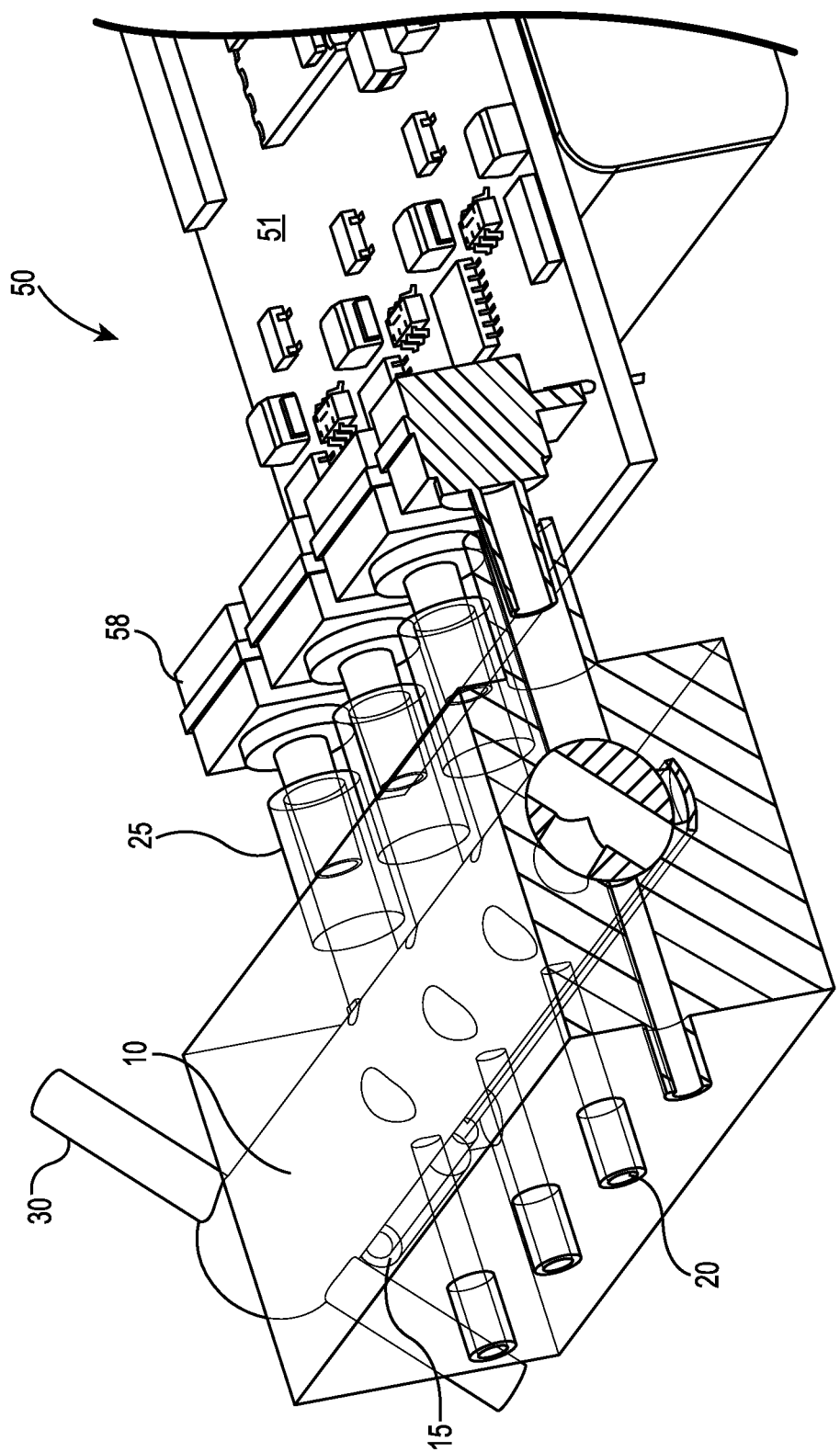
FIG. 5 shows fluidic interconnections between the ports of a multi-mode manifold when the port selector is in between a second position and a third position in accordance with various embodiments.
Figure 6:
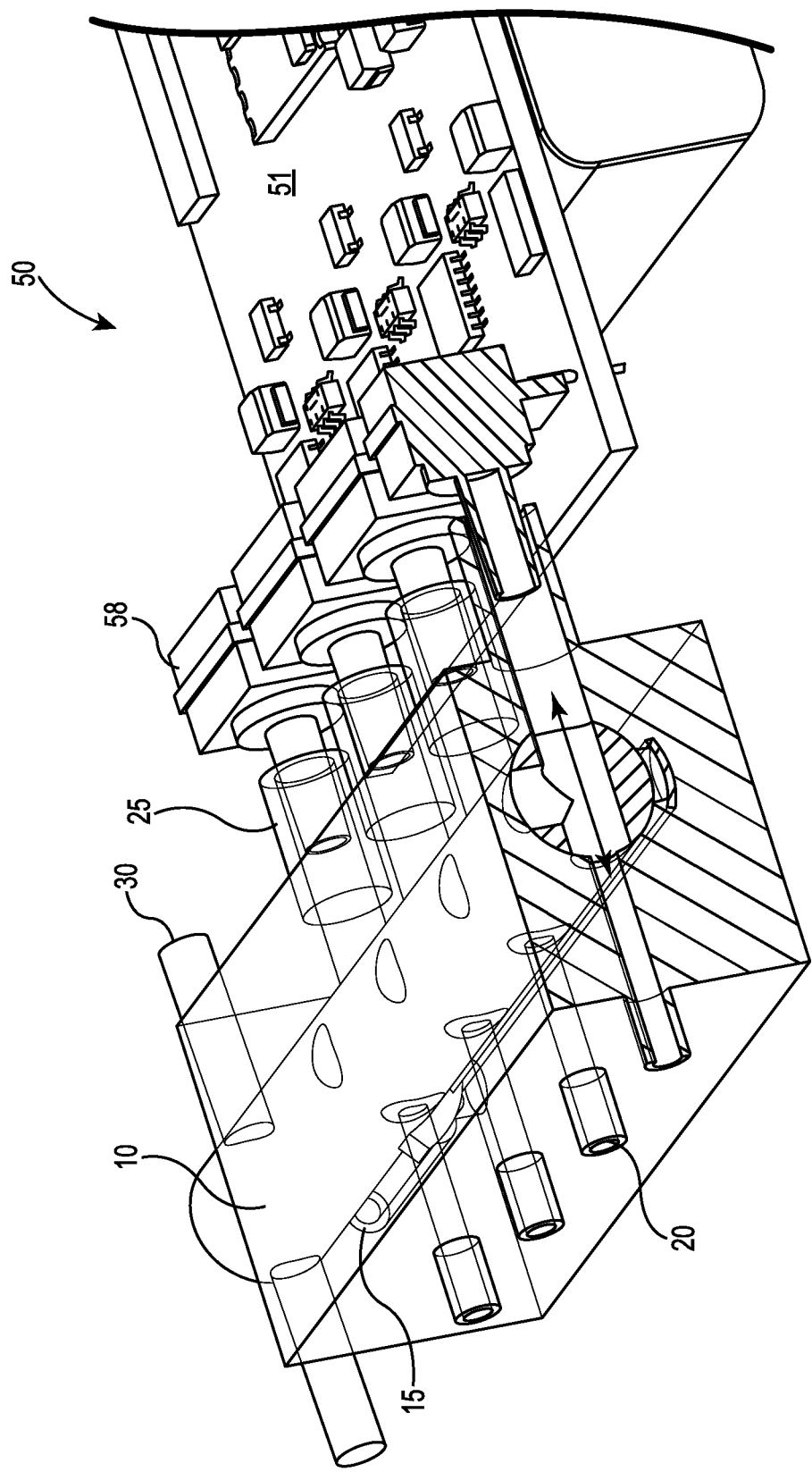
FIG. 6 shows fluidic interconnections between the ports of a multi-mode manifold when the port selector is in a third position for operating the pressure sensing system in accordance with various embodiments.

FIG. 5 shows the port selector 30 in between the up 30-U position and the forward 30-F position. In this intermediate position, the priming port 15 is disengaged (port valve 15' is closed) before the pressure transducers 58 are reconnected to the system. A port selector position between the up 30-U position and the forward 30-F position isolates the charging apparatus 40 from the motility measurement lumens 45. When the port selector 30 is advanced to the forward 30-F position, the multi-mode manifold 10 fluidly connects the pressure transducers 58 to the motility measurement lumens 45. FIG. 6 shows the port selector 30 at the forward 30-F position, allowing the system to be operated for conducting motility pressure measurements and rectal compliance testing. In this position, only the motility measurement lumens 45 (and therefore motility measurement balloons 110 of the pressure measuring catheter 100) are connected to individual pressure transducers 58. As was previously discussed, some embodiments employ a single motility measurement balloon 110, in which a single pressure transducer 58 would be fluidly coupled to the single motility measurement balloon 110 when the port selector 30 is moved to the forward 30-F position.

FIG. 7 shows various valve positions required to perform the different actions illustrated in the table of FIG. 7. Each of the actions correspond to different steps of a procedure for priming a motility manometer using a multi-mode manifold 10 in accordance with some embodiments of the disclosure.

In FIG. 7, the charging/priming device 40 is a syringe. The multi-mode manifold 10 incorporates three distinct pathways to allow priming of the system. The design allows different combinations of fluid connections between the pressure transducers 58, charging/priming apparatus 40, and motility measurement lumens 45. It will be appreciated that a multi-mode manifold 10 allows the charging/priming device 40 to be connected to the motility measurement lumens 45 independent of the pressure transducers 58. This allows the priming to stay intact when isolating the charging apparatus 40 and connecting the motility measurement lumens 45 to the pressure transducers 58. Embodiments of a motility manometer that incorporate a multi-mode manifold 10 provide a charging method without the use of a charging chamber or structure.

FIGS. 8A-8C illustrate a multi-port pneumatic connector system in accordance with embodiments of the disclosure. According to various embodiments, a multi-port manometer pneumatic connector system is incorporated in a motility manometer to allow connection of multiple channels of pressure sensing via one easy-to-connect connector. Motility manometers need to be connected to a pressure measuring source prior to use. Conventional systems contain multiple connectors which are difficult to connect and can be incorrectly connected to a wrong channel by the user. Embodiments of a multi-port pneumatic connector system provide an easy-to-connect and keyed system to ensure proper orientation of the pressure measuring source.

The embodiment shown in FIGS. 8A-8C incorporates an off-the-shelf connector housing (e.g., a standard connector manufactured by Fischer Connectors, Inc.) which is modified (customized) to incorporate a molded multi-port insert for connecting the pressure measuring source to a mating connector located on the housing of the manometer. The connector is keyed to ensure proper orientation. The mating connector located on the manometer housing contains multiple pins containing sealing rings and an internal channel for transferring the pressure from the mating connector. The pins are located in a custom housing which is assembled into an off-the-shelf mating connector. The ring seals ensure no pressure leaks during use. Various embodiments incorporate two such mating connectors (male and female) to join a motility pressure measurement catheter to a motility manometer. A multi-port manometer pneumatic connector system can be incorporated into various types of motility manometers, including esophageal, anorectal, urinary, and uteral manometers.

The multi-port pneumatic connector system illustrated in FIG. 8A is a cross sectional view of the connector system shown in FIG. 8B. The connector system includes a housing connector 101 and a mating catheter connector 400. The housing connector 101 is mounted on a side of the manometer's housing 51 as shown in the embodiment of FIG. 2A. The catheter connector 400 is mounted at the proximal end of an extension catheter 107 which is fluidly coupled to the lumens 102 of the manometer catheter's shaft 105. The housing connector 101 is configured as a male connector, and the catheter connector 400 is configured as a female connector.

The housing connector 101 includes a housing 501 within which four pins 510 are situated. Each of the pins 510 includes a fluid channel 514 and machined ring seals 512. The fluid channel 514 of each pin 510 is fluidly connected to a housing lumen 508 which terminates at a balloon lumen of the multi-port manifold of the pressure sensing device. In some embodiments, the pins 510 and the ring seals 512 are stainless steel. The catheter connector 400 includes a housing 401 within which each of the four catheter lumens 102 terminate. The core material 405 within the catheter housing 401 is SANOPRENE according to some embodiments. Each of the catheter lumens 102 terminate with a lumen connector 403 which is configured to matingly engage a corresponding housing pin 510 and fluidly connect with the fluid channel 514 of the corresponding housing pin 510. A threaded nut 505 engages corresponding threads 503 on the housing 501 to secure the pneumatic connection between the housing connector 101 and the catheter connector 400.

FIG. 8C shows a key arrangement that guarantees proper orientation between the catheter and housing connectors 400 and 101. In the embodiment illustrated in FIG. 8C, the housing 501 of the housing connector 101 includes a longitudinal key 525 which is configured to be received by a corresponding longitudinal slot (not shown) provided on the housing 401 of the catheter connector 400. It is understood that other keying features can be used other than the key and slot arrangement shown in FIG. 8C.

A multi-port manometer pneumatic connector system of the present disclosure can be incorporated in devices and systems other than manometers. It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments.

Figure 9:
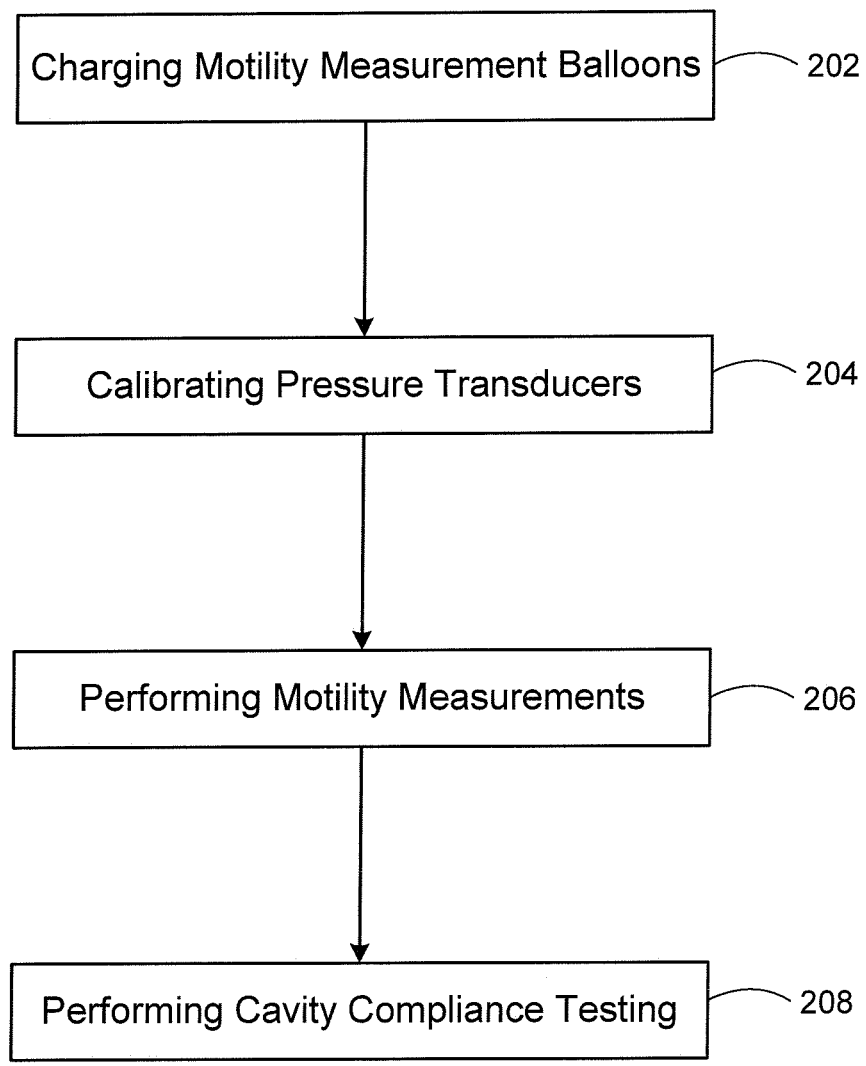
FIGS. 9 and 10 are flow charts that show a number of processes involving a pressure sensing system in accordance with various embodiments.
Figure 10:
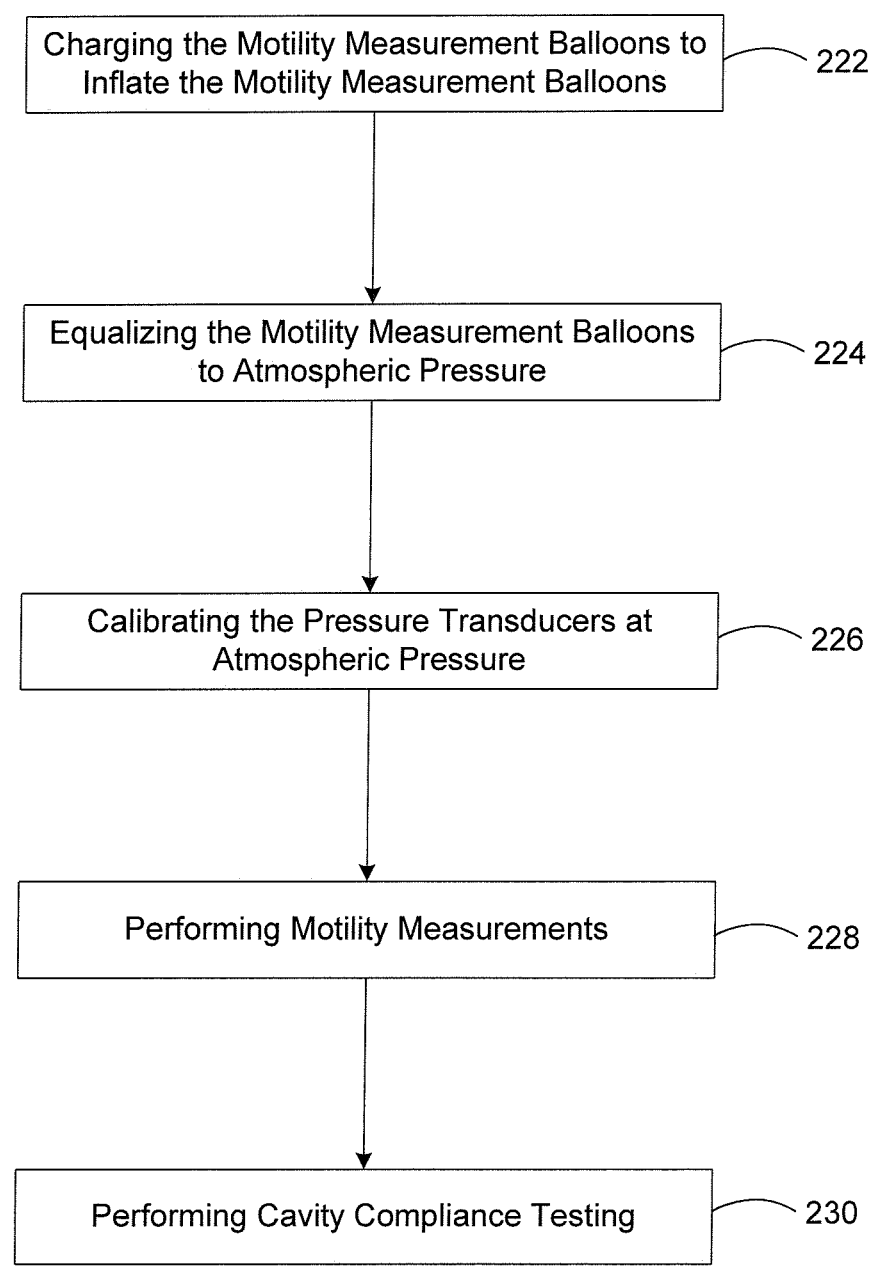

FIGS. 9 and 10 are flow charts that show a number of processes involving a pressure sensing system of the disclosure in accordance with various embodiments. Manometry testing in accordance with the embodiment shown in FIG. 9 involves charging 202 the motility measurement balloons of the catheter, and calibrating 204 the pressure sensors that are used to measure pressure changes within the motility measurement balloons. Manometry testing according to FIG. 9 also involves performing 206 motility measurements using the motility measurement balloons, and performing 208 body cavity (e.g., the rectum) compliance testing using the distension balloon of the catheter.

Manometry testing in accordance with the embodiment shown in FIG. 10 involves charging 222 the motility measurement balloons of the catheter to inflate these balloons, and subsequently equalizing 224 the motility measurement balloons and pressure transducers to atmospheric pressure. Manometry testing according to FIG. 10 also involves calibrating 226 the pressure transducers at atmospheric pressure, performing 228 motility measurements using the motility measurement balloons, and performing 230 body cavity (e.g., the rectum) compliance testing using the distension balloon of the catheter.

FIGS. 11-20 are graphical diagrams showing an icon-based user interface for a hand-held motility manometer in accordance with embodiments of the disclosure. The icon-based user interface is preferably implemented on a tablet PC and/or a medical grade PC. An icon-based user interface implemented by software for use in taking motility measurements eliminates the need for highly skilled users that are required when using traditional manometry systems. Traditional motility systems use complex software for collecting motility data. An icon-based user interface provides the clinician with intuitive visual instructions in contrast to traditional written instructions. Screen layout provides an easy to use visual interface in contrast to traditional testing methods.

Figure 11:
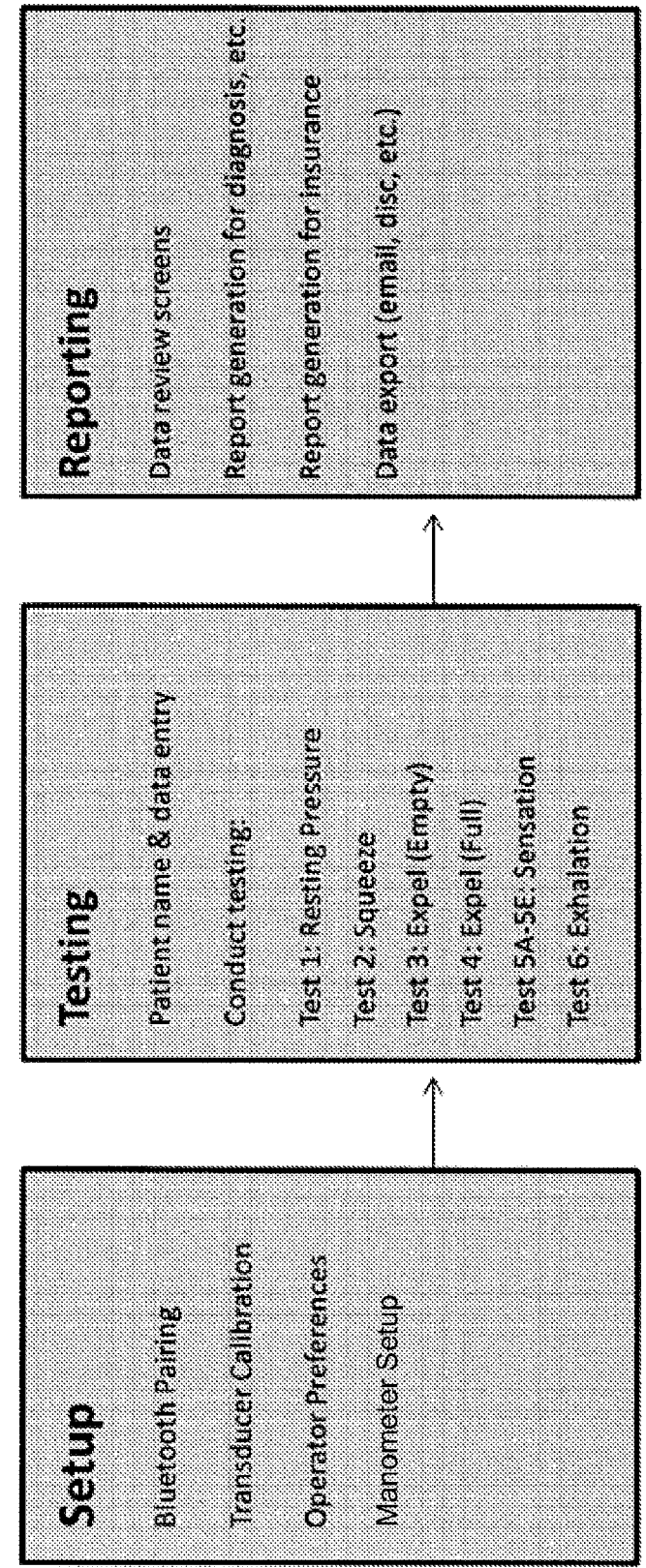

Turning now to FIG. 11, an overall work flow diagram shows three different processes involving the use of an icon-based user interface for a hand-held motility manometer in accordance with various embodiments. The overall work flow involves setup, testing, and reporting processes. The setup work flow involves pairing the pressure sensing device with the tablet PC, calibrating the pressure transducers in a manner previously discussed, inputting operator preferences by the clinician, and performing a manometer setup procedure. The clinician is guided through each of the processes by various screens presented to the user on the icon-based user interface.

Figure 12:
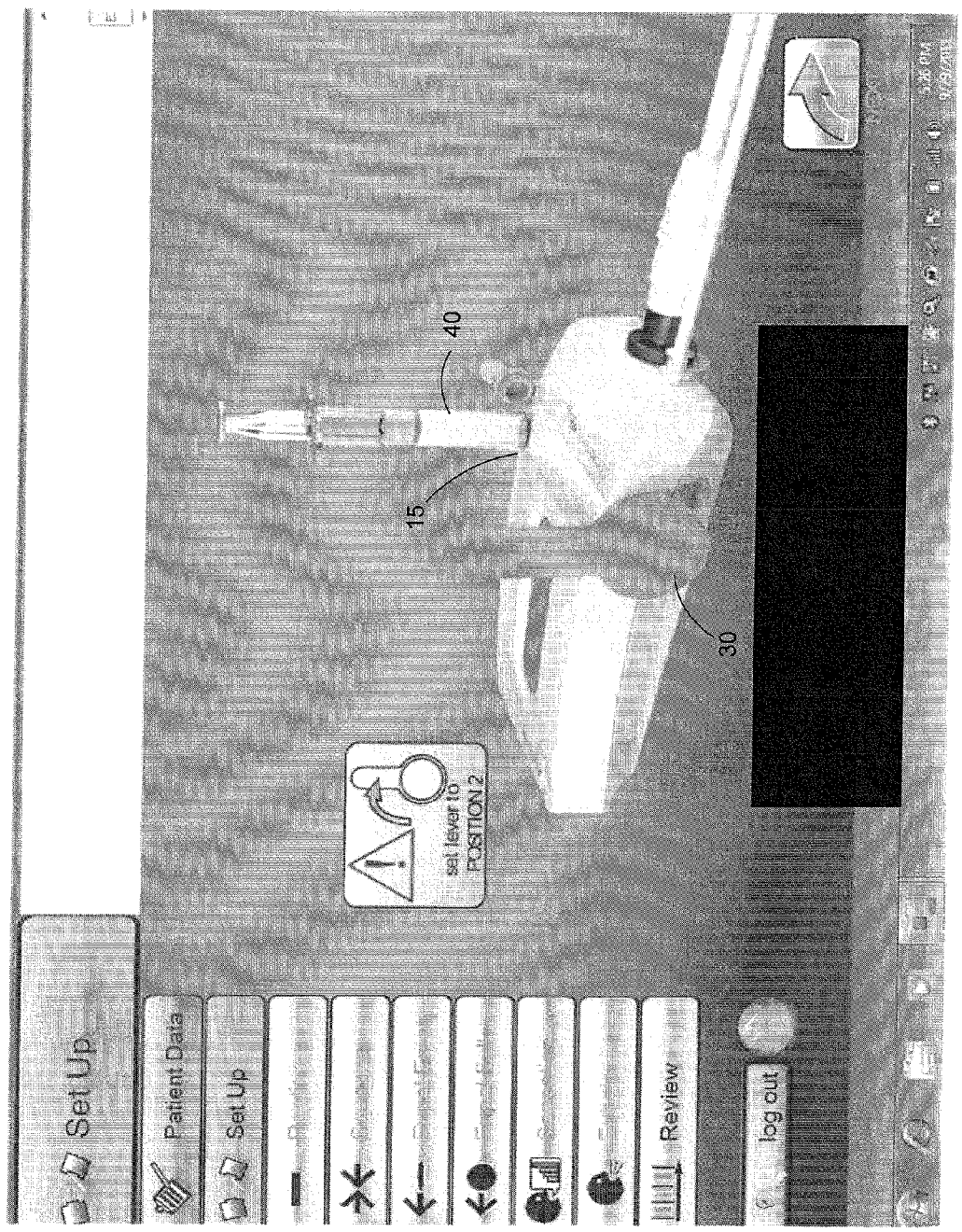
Figure 13:
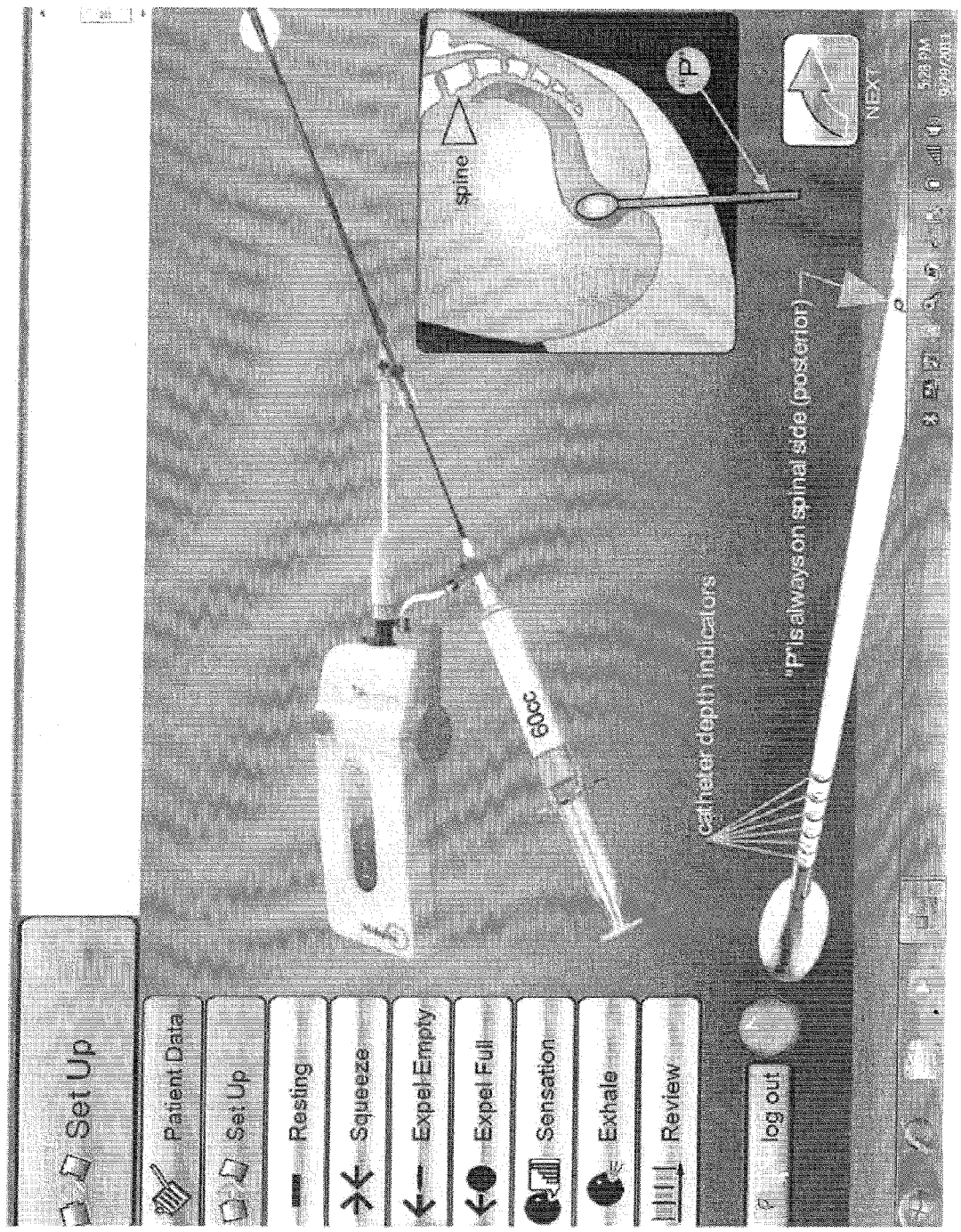
Figure 14:
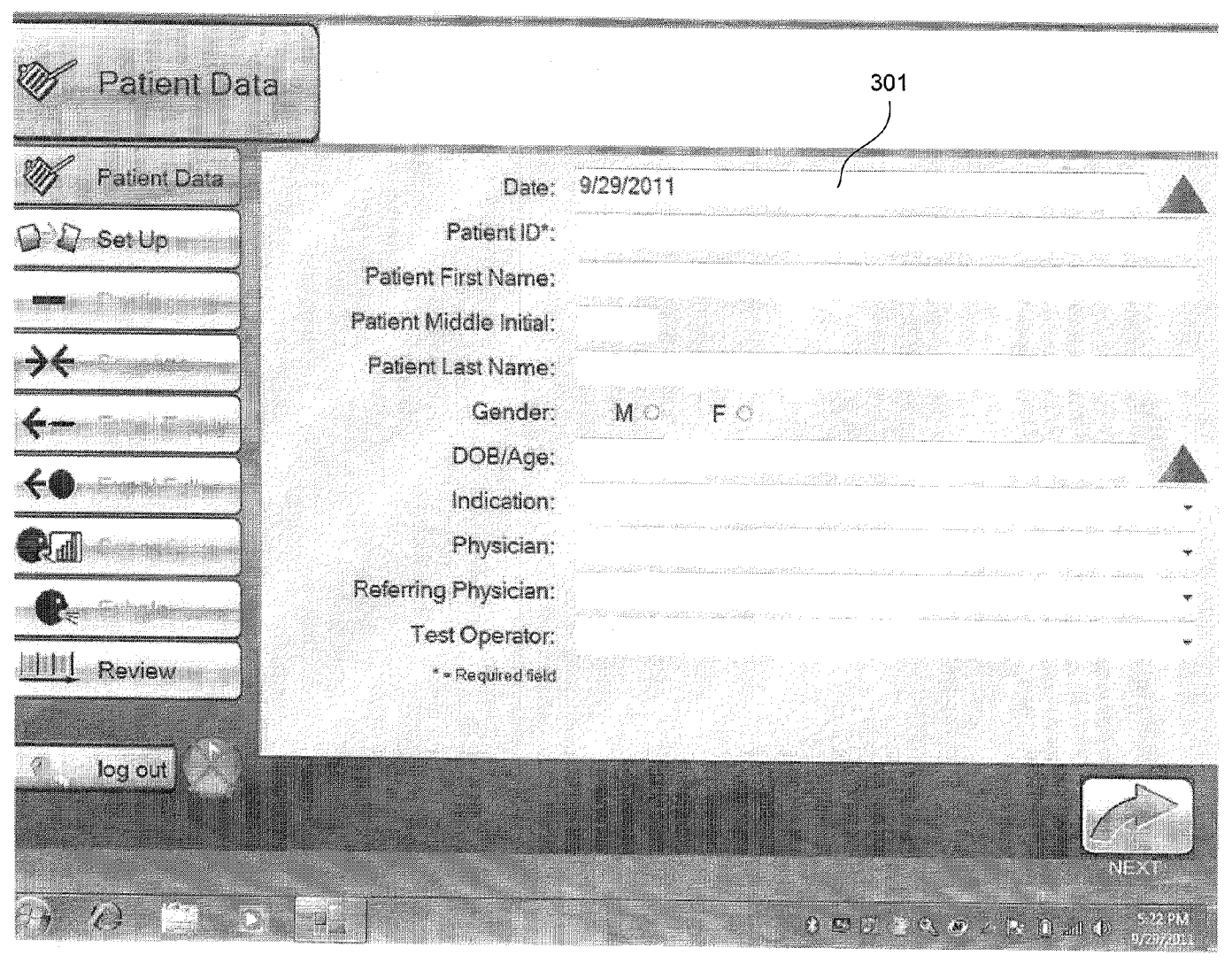
Figure 15:
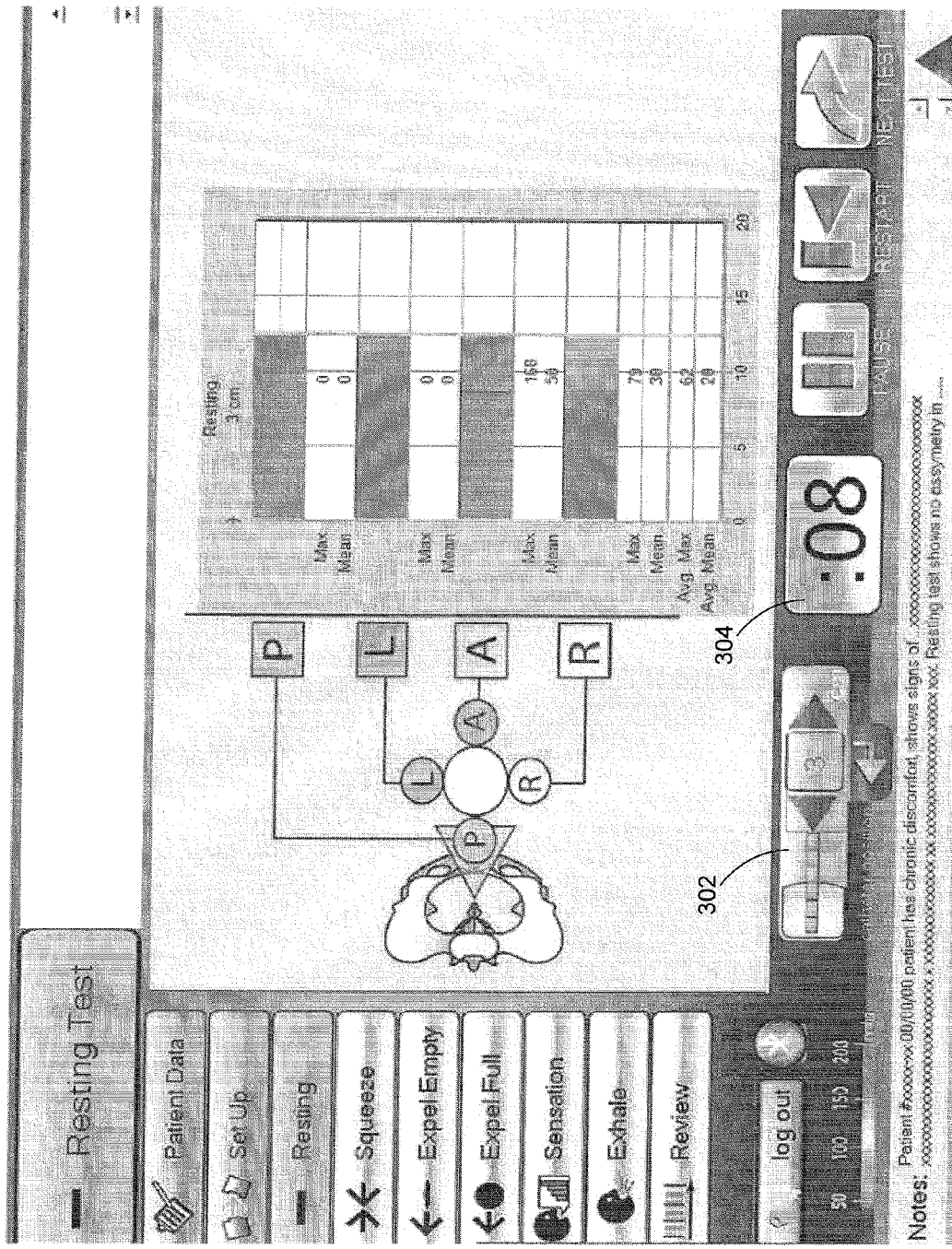
Figure 16:
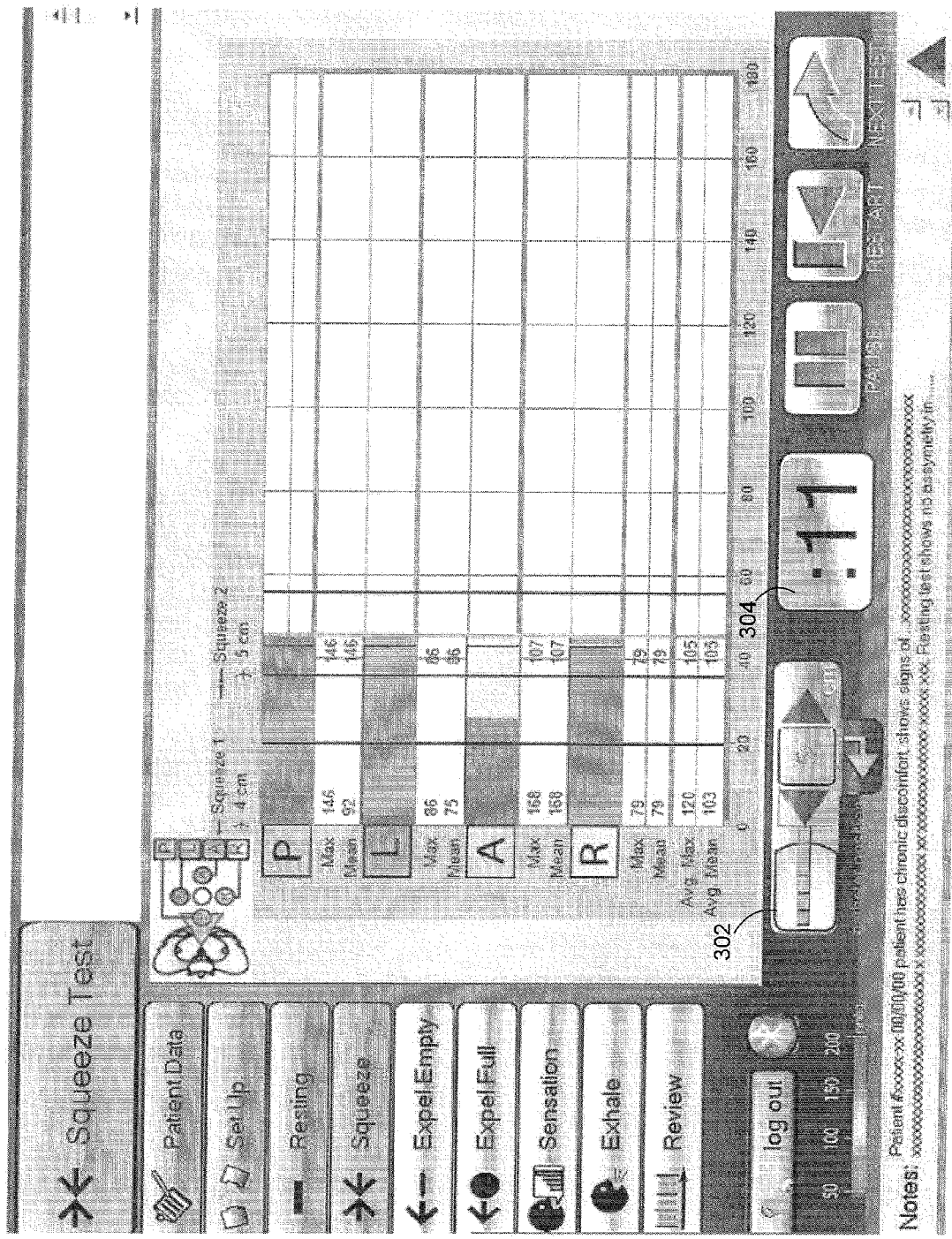
Figure 17:
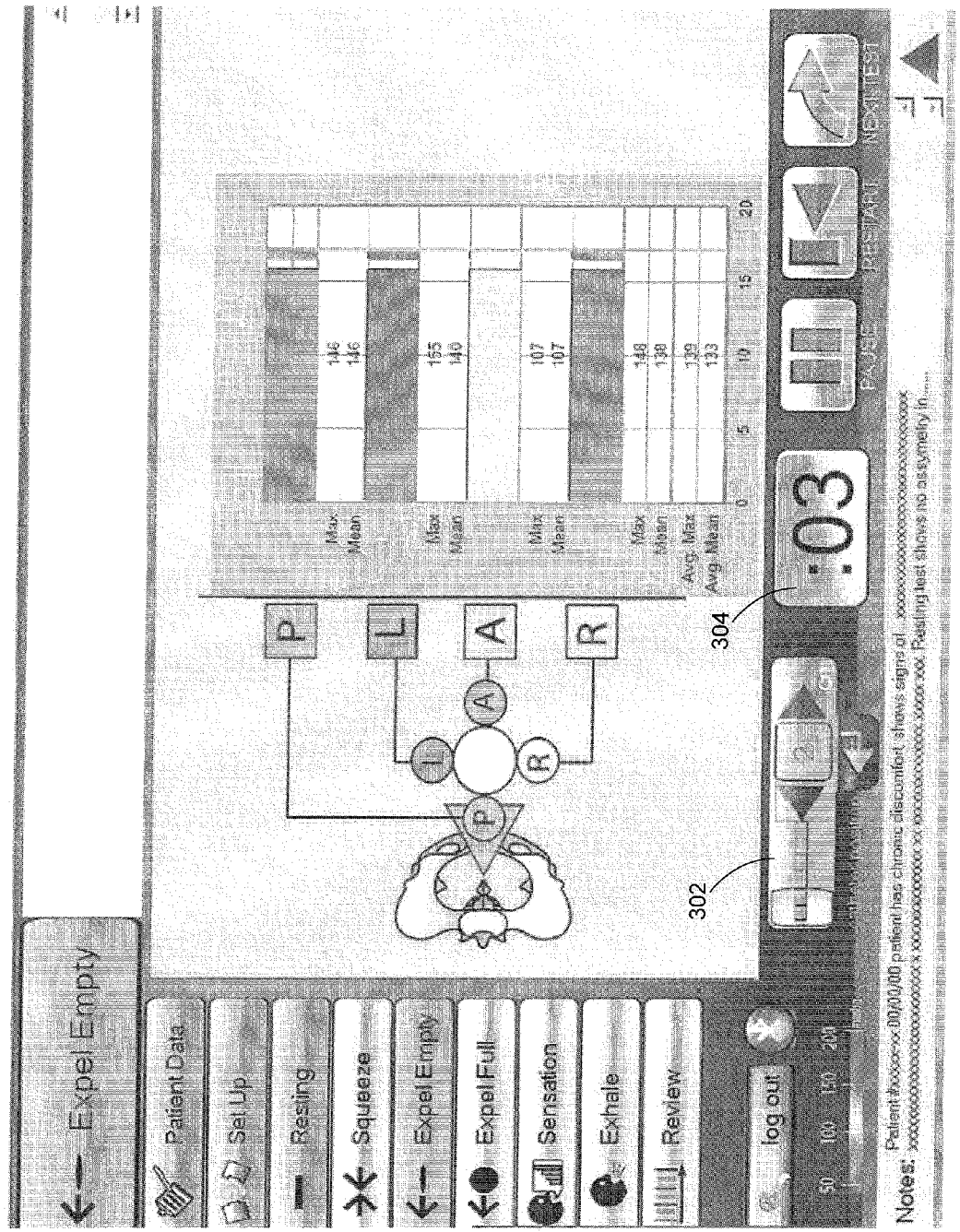

With reference to FIGS. 11 and 12, the manometer setup procedure involves priming the motility measurement balloons with a predetermined volume air (e.g., 3 cc) using a syringe 40 with the port selector lever 30 in the up position. According to various embodiments, the setup procedure also involves calibrating the pressure transducers at atmospheric pressure by moving the port selector lever 30 to the down position and zeroing out the pressure transducers. The port selector lever 30 may then be moved to the forward position, placing the manometer in the operating mode. The setup procedure further includes connecting a charging syringe filled with a predetermined volume of air (e.g., 60 cc) to the catheter's stopcock luer connector. The manometer is now ready to be inserted into the destination body cavity of the patient, which is a patient's anal canal in this illustrative embodiment. The catheter is inserted into the anal cavity until a desired depth is reached. The operator charges the distention balloon with 10 cc of air to allow pressure readings. The catheter is rotated so that the orientation indicator (e.g., "P") on the catheter shaft is facing the patient's spine. After the clinician finishes entering patient data on a patient data screen 301 shown in FIG. 14, testing may then commence.

Figure 18:
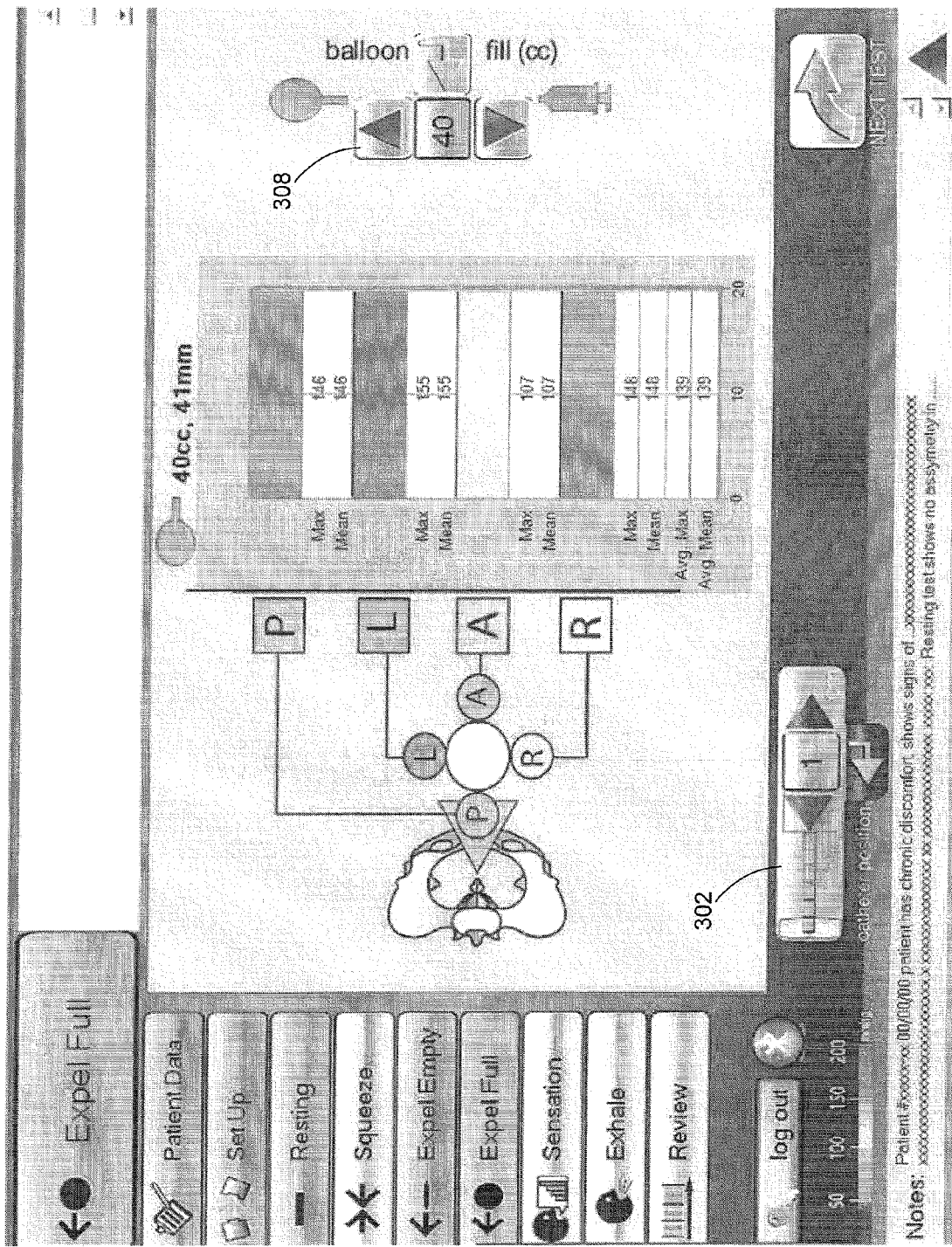
Figure 19:
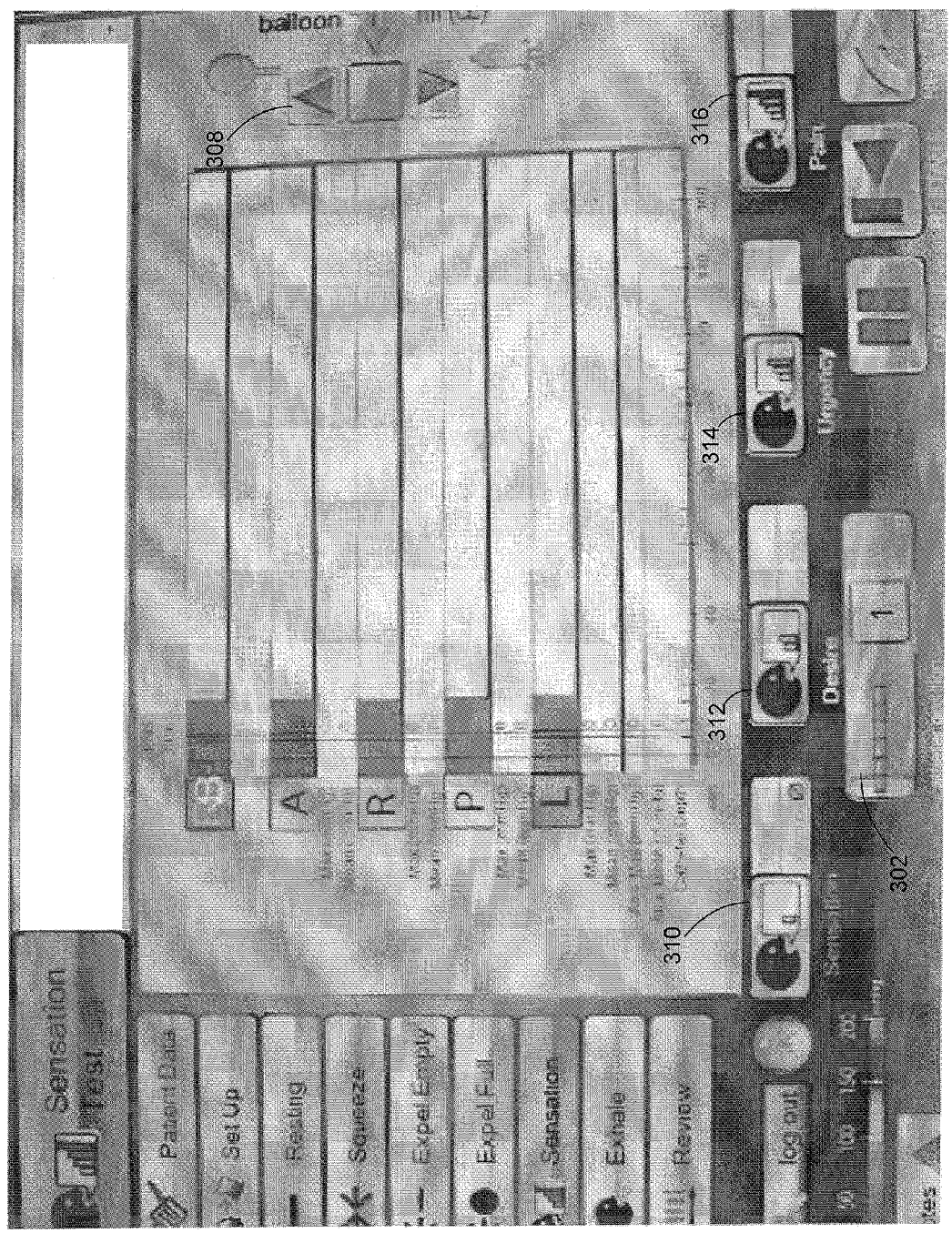
Figure 20:
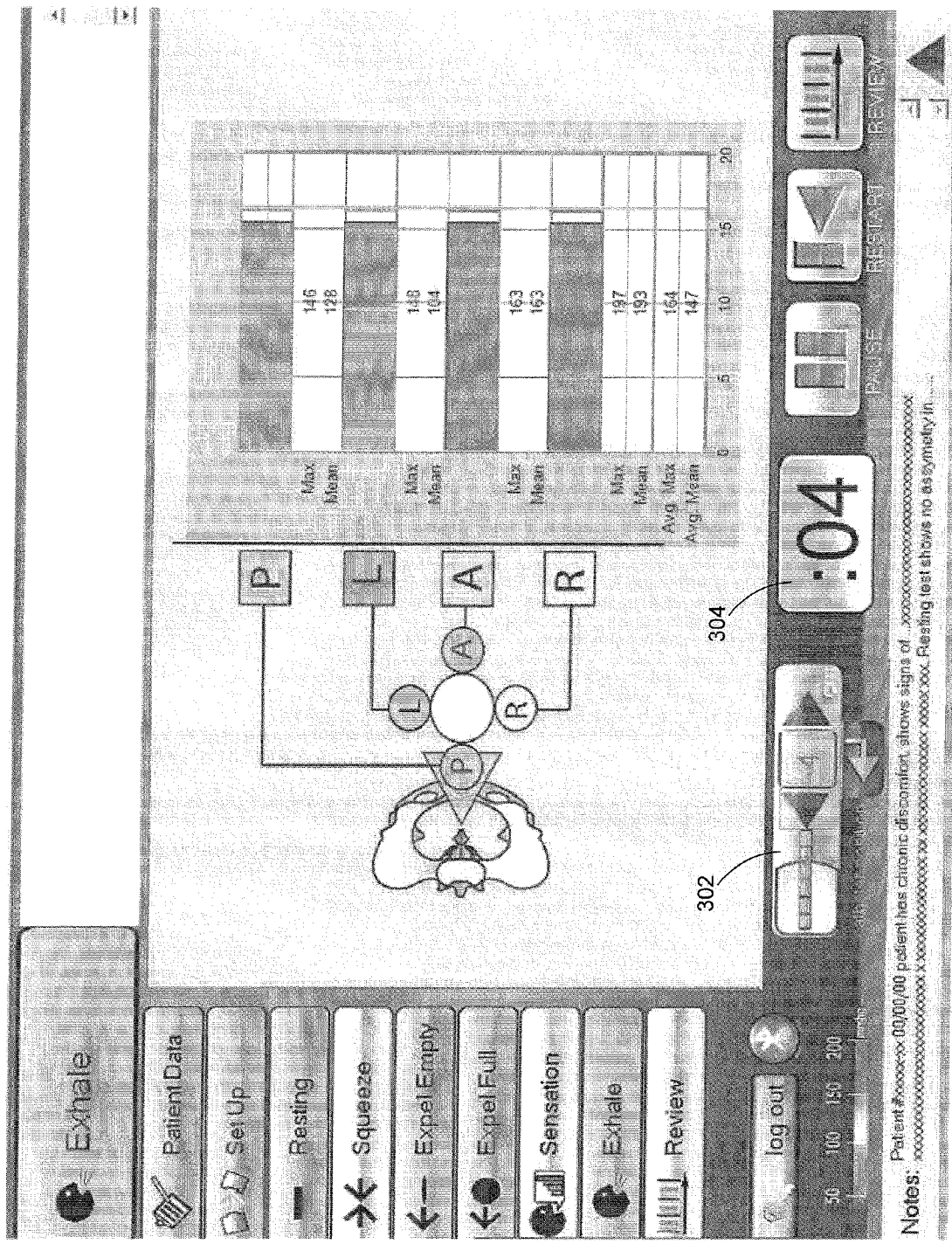

FIGS. 15-20 show screen images of the icon-based user interface during each of six phases of testing. These six tests are well known and are referred to as a resting test (FIG. 15), a squeeze test (FIG. 16), an expel empty test (FIG. 17), and expel full test (FIG. 18), a sensation test (FIG. 19), and an exhale test (FIG. 20). It is noted that the boxes labeled P, L, A, and R in FIGS. 15-20 refer to the four distinct positions of the four motility measurement balloons at posterior, left, anterior, and right positions. For each of the tests, a depth indicator 302 shows the current depth of the catheter as indicated by the depth indicators on the catheter's shaft. A timer 304 shows the elapsed time for each phase of the tests. Pressure measurements are recorded for each of the tests.

In FIGS. 18 and 19, the icon-based interface for the expel full and sensation tests include a pressure reading icon for the distention balloon. Referring particularly to FIG. 19, this interface allows the clinician to perform rectal compliance testing, which is available because the distention balloon is implemented as a compliant or semi-compliant balloon. Each of the four phases of the sensation test, sensation, desire, urgency, and pain, have discrete icons 310, 312, 314, and 316 which allows the clinician to enter or capture the distention balloon pressure at which the patient provided feedback for these four tests.

Referring once again to FIG. 11, the overall work flow involves generating a variety of reports for different recipients. The variety of reports includes reports showing data review screens, reports for diagnostics, reports for insurance purposes, and various forms of data export (e.g., email, disc, etc.).

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments.

What is claimed is:

1. A system, comprising:
   a catheter comprising a distal distension balloon and a plurality of circumferentially arranged motility measurement balloons proximal of the distension balloon;
   a manifold comprising: an elongated cylinder configured for rotation, wherein the cylinder includes an arrangement of bores contained therein; a plurality of balloon ports each configured to fluidly couple to one of the motility measurement balloons; a plurality of pressure transducer ports; and a priming port configured to open to atmospheric pressure or to receive a pressurized fluid;
   a port selector coupled to the manifold and rotatable between different positions, the manifold configured to rotate with the port selector so as to establish or prevent fluidic couplings among the balloon ports, the pressure transducer ports, and the priming port via the arrangement of bores in response to the different positions of the port selector; and
   a pressure sensing device comprising a plurality of pressure transducers each fluidly coupled to one of the plurality of pressure transducer ports,
   wherein the port selector and cylinder are configured to rotate so as to (a) permit the pressure transducers to be calibrated at the atmospheric pressure via the priming port with the port selector in a first position from among the different positions, (b) permit the motility measurement balloons to be primed via the pressurized fluid received by the priming port with the port selector in a second position from among the different positions, and (c) permit motility balloon pressure measurements to be performed by the plurality of pressure transducers via the balloon ports and the pressure transducer ports with the port selector in a third position from among the different positions, and
   wherein the priming port is fluidly decoupled from the balloon ports and the pressure transducer ports with the port selector in the third position.

2. The system of claim 1, wherein the bores are configured to align or mis-align with the balloon ports, the pressure transducer ports, and the priming port at different rotational orientations corresponding to the different positions of the port selector.

3. The system of claim 1, wherein:
   the port selector at the first position causes the manifold to fluidly couple the pressure transducer ports to the atmospheric pressure; and
   the port selector at the third position causes the manifold to fluidly couple the pressure transducer ports to the balloon ports and to fluidly decouple the priming port from the pressure transducer ports and the balloon ports.

4. The system of claim 1, wherein the distension balloon comprises a compliant balloon or a semi-compliant balloon.

5. The system of claim 1, further comprising:
   a tablet PC configured to execute software for communicating with and controlling the pressure sensing device.

6. The system of claim 1, wherein:
   the manifold, the port selector, and the pressure sensing device are supported by a housing separable from the catheter; and
   the catheter is a disposable catheter.

7. The system of claim 1, wherein:
the manifold, the port selector, and the pressure sensing device are supported by a housing separable from the catheter; and
a keyed multi-port housing connector is supported by the housing and fluidly coupled to the balloon ports of the manifold, the keyed multi-port housing connector configured to receive a keyed multi-port catheter connector of the catheter, such that alignment between key features of the keyed multi-port housing connector and the keyed multi-port catheter connector ensure proper alignment with and fluidic coupling between the balloon ports of the manifold and the motility measurement balloons of the catheter.

8. The system of claim 1, wherein the pressure sensing device is configured to perform the motility balloon pressure measurements with the pressure transducers and the motility measurement balloons initially at the atmospheric pressure with the port selector in the third position.

9. A system, comprising:
an anorectal manometry catheter comprising: a distal distension balloon comprising a compliant or semi-compliant balloon; and a plurality of circumferentially arranged motility measurement balloons proximal of the distension balloon;
a manifold comprising: an elongated cylinder configured for rotation, wherein the cylinder includes an arrangement of bores contained therein; a plurality of balloon ports each configured to fluidly couple to one of the motility measurement balloons; a plurality of pressure transducer ports; and a priming port; and
a pressure sensing device comprising: a rectal pressure transducer fluidly coupled to the distension balloon; and a plurality of pressure transducers each fluidly coupled to the plurality of pressure transducer ports,
wherein the cylinder is configured to rotate for establishing or preventing fluidic couplings among the balloon ports, the pressure transducer ports, and the priming port via the arrangement of bores so as to (a) permit the plurality of pressure transducers to be calibrated at atmospheric pressure via the priming port with the cylinder in a first position, (b) permit the plurality of motility measurement balloons to be primed with the cylinder in a second position, and (c) permit rectal compliance measurements to be performed using the rectal pressure transducer and permit motility balloon pressure measurements to be performed using the plurality of pressure transducers via the balloon ports and the pressure transducer ports with the cylinder in a third position,
wherein the priming port is fluidly decoupled from the balloon ports and the pressure transducer ports with the cylinder in the third position.

10. The system of claim 9, wherein the distension balloon comprises a semi-compliant balloon.

11. The system of claim 9, further comprising an external computing device configured to communicate with and control the pressure sensing device.

12. The system of claim 9, wherein:
the manifold and the pressure sensing device are supported by a housing separable from the catheter; and
a keyed multi-port housing connector is supported by the housing and fluidly coupled to the balloon ports of the manifold, the keyed multi-port housing connector configured to receive a keyed multi-port catheter connector of the catheter, such that alignment between key features of the keyed multi-port housing connector and the keyed multi-port catheter connector ensure proper alignment with and fluidic coupling between the plurality of balloon ports of the manifold and the plurality of motility measurement balloons of the catheter.

13. The system of claim 9, wherein the pressure sensing device is configured to perform the rectal compliance measurements with the plurality of pressure transducers and the plurality of motility measurement balloons initially at the atmospheric pressure with the cylinder in the third position.

* * * * *